(12) United States Patent
Sampietro et al.

(10) Patent No.: US 11,395,825 B2
(45) Date of Patent: Jul. 26, 2022

(54) COMPOSITIONS AND METHODS FOR TREATING EYES AND METHODS OF PREPARATION

(71) Applicant: Ocular Science, Inc., Manhattan Beach, CA (US)

(72) Inventors: Anthony Sampietro, Los Angeles, CA (US); Damien Goldberg, Manhattan Beach, CA (US); Amy Frost, Stevensville, MT (US); Brian Holdorf, Missoula, MT (US)

(73) Assignee: OCULAR SCIENCE, INC., Manhattan Beach, CA (US)

( * ) Notice: Subject to any disclaimer, the term of this patent is extended or adjusted under 35 U.S.C. 154(b) by 97 days.

(21) Appl. No.: 16/751,177

(22) Filed: Jan. 23, 2020

(65) Prior Publication Data

US 2020/0222428 A1 Jul. 16, 2020

Related U.S. Application Data

(63) Continuation of application No. 15/971,936, filed on May 4, 2018, now abandoned.

(60) Provisional application No. 62/646,287, filed on Mar. 21, 2018, provisional application No. 62/621,299, filed on Jan. 24, 2018, provisional application No. 62/501,390, filed on May 4, 2017.

(51) Int. Cl.
| | |
|---|---|
| *A61K 31/137* | (2006.01) |
| *A61K 31/167* | (2006.01) |
| *A61K 31/407* | (2006.01) |
| *A61K 9/00* | (2006.01) |
| *A61P 27/02* | (2006.01) |
| *A61K 31/573* | (2006.01) |
| *A61K 31/5575* | (2006.01) |
| *A61K 31/496* | (2006.01) |
| *A61K 31/4709* | (2006.01) |
| *A61K 31/382* | (2006.01) |
| *A61K 31/498* | (2006.01) |
| *A61K 31/216* | (2006.01) |
| *A61K 31/5377* | (2006.01) |

(52) U.S. Cl.
CPC .......... *A61K 31/573* (2013.01); *A61K 9/0048* (2013.01); *A61K 31/137* (2013.01); *A61K 31/167* (2013.01); *A61K 31/216* (2013.01); *A61K 31/382* (2013.01); *A61K 31/407* (2013.01); *A61K 31/4709* (2013.01); *A61K 31/496* (2013.01); *A61K 31/498* (2013.01); *A61K 31/5377* (2013.01); *A61K 31/5575* (2013.01); *A61P 27/02* (2018.01)

(58) Field of Classification Search
CPC .. A61K 9/0048; A61K 31/137; A61K 31/167; A61K 31/407; A61K 2300/00; A61P 23/02; A61P 27/02–14
See application file for complete search history.

(56) References Cited

U.S. PATENT DOCUMENTS

| | | |
|---|---|---|
| 6,548,079 B1 | 4/2003 | Kuhn |
| 6,551,584 B2 | 4/2003 | Bandyopadhyay |
| 6,716,830 B2 | 4/2004 | Cagle |
| 6,740,664 B2 | 5/2004 | Cagle |
| 7,612,115 B2 | 11/2009 | Suzuki |
| 7,971,070 B2 | 6/2011 | Lotspiech et al. |
| 8,263,125 B2 | 9/2012 | Vaya |
| 8,268,352 B2 | 9/2012 | Vaya |
| 8,470,784 B2 | 6/2013 | Liu |
| 8,680,078 B2 | 3/2014 | Aleo |
| 8,778,999 B2 | 7/2014 | Hosseini |
| 9,016,221 B2 | 4/2015 | Brennan |
| 9,087,145 B2 | 7/2015 | Ballou |
| 9,271,866 B2 | 3/2016 | Humayun |
| 9,278,101 B2 | 3/2016 | Demopulos |
| 9,308,124 B2 | 4/2016 | Humayun |
| 9,554,968 B2 | 1/2017 | Weikart |
| 9,662,450 B2 | 5/2017 | Jones |
| 2002/0035264 A1 | 3/2002 | Kararli |

(Continued)

FOREIGN PATENT DOCUMENTS

| | | | |
|---|---|---|---|
| EP | 2036538 A1 | 3/2009 | |
| EP | 2127638 A1 * | 12/2009 | ......... A61K 31/5575 |

OTHER PUBLICATIONS

Garcia-Lopez et al., Efficacy and tolerability of fixed-combination bimatoprost/timolol versus fixed-combination dorzolamide/brimonidine/timolol in patients with primary open-angle glaucoma or ocular hypertension: a multicenter, prospective, crossover study, BMC Ophthalmology, 14 (161), pp. 1-12, 2014.

*Primary Examiner* — Theodore R. Howell
(74) *Attorney, Agent, or Firm* — Wilson Sonsini Goodrich & Rosati

(57) ABSTRACT

Pharmaceutical compositions, methods for treating various issues of the eyes, and methods of preparing such compositions are described. These pharmaceutical compositions may be for treating glaucoma, in preparation of eye surgery, during eye surgery, various post-op care (e.g., after cataract surgery, laser eye surgery, and the like), for treating dry eyes, and/or for promoting eyelash growth. These pharmaceutical compositions may comprise such active ingredients (APIs) as: timolol, latanoprost, brimonidine tartrate, dorzolamide, moxifloxacin HCl, dexamethasone PO4, phenylephrine HCl, lidocaine HCl, ketorolac tromethamine, bromfenac, prednisolone PO4, gatifloxacin, amniotic cytokine extract (ACE), prostaglandin E2 (PGE2), and combinations thereof.

17 Claims, 22 Drawing Sheets

(56) References Cited

U.S. PATENT DOCUMENTS

| | | |
|---|---|---|
| 2003/0114830 A1* | 6/2003 | Guerrero ............... A61F 9/0017 604/521 |
| 2004/0072809 A1 | 4/2004 | Demopulos |
| 2005/0043214 A1 | 2/2005 | Goeme |
| 2005/0261641 A1 | 11/2005 | Warchol |
| 2006/0183698 A1 | 8/2006 | Abelson |
| 2007/0211212 A1 | 9/2007 | Bennwik |
| 2009/0048261 A1 | 2/2009 | Montano |
| 2009/0069345 A1 | 3/2009 | Montano |
| 2010/0063017 A1 | 3/2010 | Rajan |
| 2010/0105643 A1 | 4/2010 | Soil |
| 2010/0227928 A1 | 9/2010 | Hosseini |
| 2010/0311705 A1 | 12/2010 | Demopulos |
| 2011/0294768 A1 | 12/2011 | Rajan |
| 2012/0184552 A1 | 7/2012 | Nakajima |
| 2012/0316143 A1 | 12/2012 | Soll |
| 2013/0020227 A1 | 1/2013 | Stack |
| 2013/0035338 A1 | 2/2013 | Tang |
| 2013/0041241 A1 | 2/2013 | Felts |
| 2013/0065869 A1 | 3/2013 | Demopulos |
| 2013/0079344 A1 | 3/2013 | Demopulos |
| 2013/0165419 A1 | 6/2013 | Lindstrom |
| 2013/0338126 A1 | 12/2013 | Rajan |
| 2014/0024642 A1 | 1/2014 | Vejarano Restrepo |
| 2014/0187497 A1 | 7/2014 | Jacob |
| 2014/0213561 A1 | 7/2014 | Rajan |
| 2014/0221326 A1 | 8/2014 | Demopulos |
| 2014/0235597 A1 | 8/2014 | Demopulos |
| 2014/0235691 A1* | 8/2014 | Demopulos ............. A61P 29/00 514/413 |
| 2015/0119440 A1 | 4/2015 | Karolchyk |
| 2015/0164882 A1 | 6/2015 | Dilzer |
| 2015/0335704 A1 | 11/2015 | Karolchyk |
| 2016/0101178 A1 | 4/2016 | Wilson |
| 2016/0106761 A1 | 4/2016 | Demopulos |
| 2016/0175323 A1 | 6/2016 | Wiley |
| 2016/0243031 A1 | 8/2016 | Wiley |
| 2016/0279055 A1 | 9/2016 | Liegner |
| 2016/0354308 A1 | 12/2016 | Karolchyk |
| 2017/0049721 A1 | 2/2017 | Karolchyk |
| 2017/0100412 A1 | 4/2017 | Demopulos |
| 2017/0312295 A1 | 11/2017 | Demopulos |
| 2018/0055790 A1 | 3/2018 | Karolchyk |

* cited by examiner

Baseline Characteristics

|  |  | Control (N=23) | IP (N=28) |
|---|---|---|---|
| Female<br>Male | N (%) | 17 (74%)<br>6 (26%) | 14 (50%)<br>14 (50%) |
| Age | N<br>Mean (SD)<br>Min, Max | 23<br>78.3 (11.68)<br>52, 98 | 28<br>74.8 (11.20)<br>43, 94 |
| Morning IOP | N<br>Mean (SD)<br>Min, Max | 23<br>18.1 (4.98)<br>11, 28 | 28<br>19.5 (6.59)<br>13, 47 |
| Pachymetry | N<br>Mean (SD)<br>Min, Max | 23<br>554.3 (27.34)<br>515, 614 | 28<br>549.1 (86.45)<br>415, 953 |
| ON Ratio | N<br>Mean (SD)<br>Min, Max | 22<br>0.68 (0.213)<br>0.1, 0.9 | 28<br>0.70 (0.177)<br>0.3, 0.9 |

FIG. 3

Morning IOP Change From Baseline

| | Control | IP | IP minus Control | P-value* |
|---|---|---|---|---|
| Day 7 | N<br>LS Mean (SE)<br>95% CI<br>LS Mean (95% CI) | 23<br>-1.7 (0.62)<br>(-2.9, -0.4) | 28<br>-2.8 (0.55)<br>(-3.9, -1.7) | -1.1 (-2.7, 0.4) | 0.147 |
| Day 30 | N<br>LS Mean (SE)<br>95% CI<br>LS Mean (95% CI) | 22<br>-1.8 (0.70)<br>(-3.2, -0.4) | 28<br>-3.6 (0.61)<br>(-4.8, -2.4) | -1.8 (-3.5, 0.0) | 0.044 |
| Day 60 | N<br>LS Mean (SE)<br>95% CI<br>LS Mean (95% CI) | 21<br>-1.1 (0.65)<br>(-2.4, 0.2) | 28<br>-4.2 (0.54)<br>(-5.2, -3.1) | -3.1 (-4.6, -1.5) | <0.001 |
| Day 90 | N<br>LS Mean (SE)<br>95% CI<br>LS Mean (95% CI) | 19<br>-2.3 (0.81)<br>(-3.9, -0.7) | 28<br>-4.3 (0.61)<br>(-5.5, -3.1) | -2.0 (-3.8, -0.1) | 0.035 |

FIG. 6

Visual Acuity (logMar) Change From Baseline

| | | Treatment | | P-value* |
|---|---|---|---|---|
| | | Control | IP | |
| Day 7 | N<br>LS Mean (SE)<br>95% CI | 23<br>-0.02 (0.01)<br>(-0.04, 0.01) | 28<br>-0.02 (0.01)<br>(-0.04, 0.01) | 0.954 |
| Day 30 | N<br>LS Mean (SE)<br>95% CI | 22<br>-0.02 (0.01)<br>(-0.04, 0.00) | 28<br>-0.01 (0.01)<br>(-0.03, 0.01) | 0.494 |
| Day 60 | N<br>LS Mean (SE)<br>95% CI | 21<br>-0.04 (0.03)<br>(-0.10, 0.02) | 28<br>-0.01 (0.02)<br>(-0.06, 0.04) | 0.379 |
| Day 90 | N<br>LS Mean (SE)<br>95% CI | 19<br>0.02 (0.02)<br>(-0.02, 0.07) | 28<br>-0.01 (0.02)<br>(-0.04, 0.02) | 0.188 |

* ANCOVA

FIG. 9

UCDVA Frequencies

|  |  | Control | IP |
|---|---|---|---|
| Screening | 20/15 | 8 (16%) | 1 (2%) |
|  | 20/20 | 40 (82%) | 39 (75%) |
|  | 20/25 | 0 | 10 (19%) |
|  | 20/30 | 1 (2%) | 1 (2%) |
|  | 20/40 | 0 | 1 (2%) |
| Day 1 | 20/15 | 19 (39%) | 5 (10%) |
|  | 20/20 | 23 (47%) | 35 (69%) |
|  | 20/25 | 3 (6%) | 8 (16%) |
|  | 20/30 | 1 (2%) | 2 (4%) |
|  | 20/40 | 1 (2%) | 1 (2%) |
|  | 20/70 | 1 (2%) | 0 |
|  | 20/200 | 1 (2%) | 0 |
| Day 7 | 20/15 | 20 (43%) | 5 (10%) |
|  | 20/20 | 24 (51%) | 35 (71%) |
|  | 20/25 | 0 | 6 (12%) |
|  | 20/30 | 1 (2%) | 1 (2%) |
|  | 20/40 | 0 | 2 (4%) |
|  | 20/50 | 1 (2%) | 0 |
|  | 20/70 | 1 (2%) | 0 |
| Day 30 | 20/15 | 24 (52%) | 7 (14%) |
|  | 20/20 | 20 (43%) | 41 (80%) |
|  | 20/25 | 0 | 2 (4%) |
|  | 20/30 | 0 | 1 (2%) |
|  | 20/70 | 2 (4%) | 0 |

FIG. 10

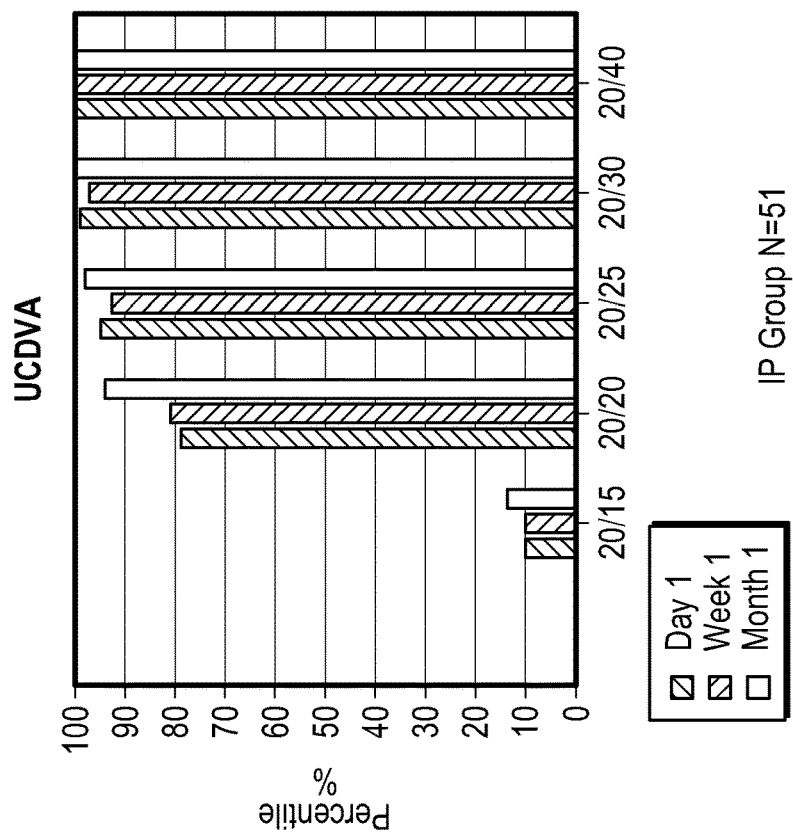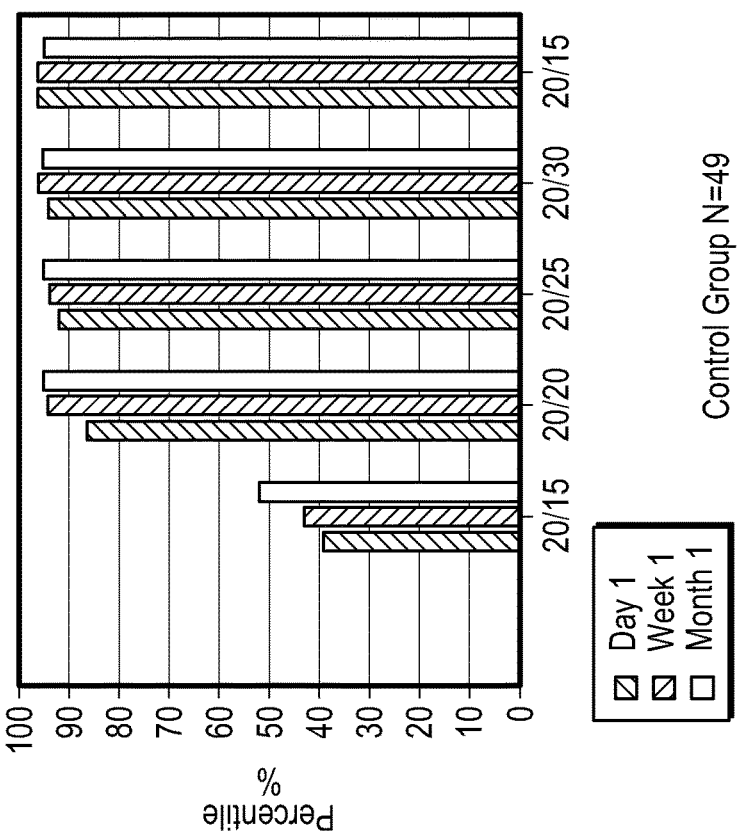
FIG. 11

UCVA Outcomes Summary

| | | Treatment | | P-value* |
|---|---|---|---|---|
| | | Control | IP | |
| Day 1 | N<br>LS Mean (SE)<br>95% CI | 49<br>0.00 (0.03)<br>(-0.05, 0.05) | 51<br>0.00 (0.03)<br>(-0.05, 0.05) | 0.933 |
| Day 7 | N<br>LS Mean (SE)<br>95% CI | 47<br>-0.02 (0.02)<br>(-0.05, 0.02) | 49<br>0.00 (0.02)<br>(-0.03, 0.04) | 0.489 |
| Day 30 | N<br>LS Mean (SE)<br>95% CI | 46<br>-0.03 (0.02)<br>(-0.07, 0.01) | 51<br>-0.03 (0.02)<br>(-0.07, 0.01) | 0.929 |

*ANCOVA

FIG. 12

AC Cell

|  |  | Control (N=52) | IP (N=49) |
|---|---|---|---|
| Screening | None<br>>0 | 49 (100%)<br>0 | 52 (100%)<br>0 |
| Day 1 | None<br>>0 | 49 (100%)<br>0 | 51 (100%)<br>0 |
| Day 7 | None<br>>0 | 47 (100%)<br>0 | 49 (100%)<br>0 |
| Day 30 | None<br>>0 | 46 (100%)<br>0 | 51 (100%)<br>0 |

FIG. 13

AC Flare

|  |  | Control (N=48) | IP (N=52) |
|---|---|---|---|
| Screening | None<br>0.5<br>>0.5 | 48 (98%)<br>1 (2%)<br>0 | 52 (100%)<br>0<br>0 |
| Day 1 | None<br>>0 | 49 (100%)<br>0 | 51 (100%)<br>0 |
| Day 7 | None<br>>0 | 47 (100%)<br>0 | 49 (100%)<br>0 |
| Day 30 | None<br>>0 | 46 (100%)<br>0 | 51 (100%)<br>0 |

FIG. 14

Total Corneal Staining

| | Control | IP | IP-Control | P-value* |
|---|---|---|---|---|
| Day 1<br>N<br>LS Mean (SE)<br>95% CI<br>LS Mean (95% CI) | 49<br>0.2 (0.11)<br>(0.0, 0.4) | 51<br>0.3 (0.10)<br>(0.1, 0.5) | 0.1 (-0.2, 0.4) | 0.495 |
| Day 7<br>N<br>LS Mean (SE)<br>95% CI<br>LS Mean (95% CI) | 47<br>0.2 (0.16)<br>(-0.1, 0.6) | 49<br>0.4 (0.15)<br>(0.1, 0.7) | 0.1 (-0.3, 0.6) | 0.525 |
| Day 30<br>N<br>LS Mean (SE)<br>95% CI<br>LS Mean (95% CI) | 46<br>0.2 (0.11)<br>(0.0, 0.4) | 51<br>0.0 (0.10)<br>(-0.2, 0.2) | -0.2 (-0.5, 0.1) | 0.262 |

* Wilcoxon Rank Sum test

FIG. 15

IOP Change from Baseline

| | | Control | IP | IP-Control | P-value* |
|---|---|---|---|---|---|
| Day 1 | N<br>LS Mean (SE)<br>95% CI<br>LS Mean (95% CI) | 11<br>-1.0 (0.97)<br>(-3.1, 1.1) | 6<br>-1.6 (0.95)<br>(-3.7, 0.5) | -0.6 (-2.7, 1.5) | 0.555 |
| Day 7 | N<br>LS Mean (SE)<br>95% CI<br>LS Mean (95% CI) | 14<br>-2.2 (0.57)<br>(-3.4, -1.1) | 15<br>-1.6 (0.40)<br>(-2.4, -0.7) | 0.6 (-0.7, 2.0) | 0.322 |
| Day 30 | N<br>LS Mean (SE)<br>95% CI<br>LS Mean (95% CI) | 46<br>-1.0 (0.25)<br>(-1.5, -0.5) | 16<br>-1.7 (0.38)<br>(-2.4, -0.9) | 0.6 (-1.5, 0.2) | 0.138 |

* Wilcoxon Rank Sum test

FIG. 16

Summary of Week 4 Study Results

| Change | | | 30 Day and 90 Day Combined | |
|---|---|---|---|---|
| | | | Baseline | Week 4 |
| Eye Dryness/Irritation (VAS 0-100) | N<br>Mean (SD)<br>95% CI | 53<br>69.5 (18.44)<br>(64.4, 74.5) | 50<br>44.0 (23.95)<br>(37.2, 50.8) | 50<br>-23.8 (23.00)*<br>(-30.3, -17.3) |
| Total Corneal Staining (0-20) | N<br>Mean (SD)<br>95% CI | 54<br>7.9 (4.89)<br>(6.5, 9.2) | 50<br>4.0 (3.77)<br>(2.9, 5.1) | 50<br>-3.7 (3.10)*<br>(-4.6, -2.8) |
| Total Conjunctival Staining (0-24) | N<br>Mean (SD)<br>95% CI | 54<br>6.8 (4.72)<br>(5.5, 8.1) | 50<br>5.0 (4.91)<br>(3.6, 6.4) | 50<br>-2.0 (4.13)*<br>(-3.1, -0.8) |
| Visual Acuity (LogMar) | N<br>Mean (SD)<br>95% CI | 48<br>0.23 (0.209)<br>(0.17, 0.29) | 46<br>0.18 (0.170)<br>(0.13, 0.23) | 46<br>-0.05 (0.092)*<br>(-0.08, -0.02) |

* denotes p<0.01, via paired t-test

FIG. 17

Summary of Week 12 Study Results

| | Baseline | Week 12 | Change |
|---|---|---|---|
| Eye Dryness/Irritation (VAS 0-100) | N<br>Mean (SD)<br>95% CI | 38<br>68.3 (19.77)<br>(61.8, 74.8) | 21<br>36.7 (22.77)<br>(26.3, 47.0) | 21<br>-37.4 (23.03)*<br>(-47.9, -26.9) |
| Total Corneal Staining (0-20) | N<br>Mean (SD)<br>95% CI | 38<br>9.4 (4.58)<br>(7.9, 10.9) | 21<br>1.3 (1.38)<br>(0.7, 2.0) | 21<br>-6.4 (3.10)*<br>(-7.8, -4.9) |
| Total Conjunctival Staining (0-24) | N<br>Mean (SD)<br>95% CI | 38<br>5.9 (3.49)<br>(4.7, 7.0) | 21<br>1.7 (2.01)<br>(0.8, 2.6) | 21<br>-4.4 (3.03)*<br>(-5.7, -3.0) |
| Visual Acuity (LogMar) | N<br>Mean (SD)<br>95% CI | 38<br>0.26 (0.220)<br>(0.19, 0.34) | 21<br>0.14 (0.140)<br>(0.08, 0.21) | 21<br>-0.09 (0.113)*<br>(-0.14, -0.04) |

\* denotes p<0.001, via paired t-test

FIG. 18

COMPOSITIONS AND METHODS FOR TREATING EYES AND METHODS OF PREPARATION

PRIORITY NOTICE

The present application is a continuation of application Ser. No. 15/971,936, filed on May 4, 2018, which claims priority to Provisional Application No. 62/646,287, filed Mar. 21, 2018; Provisional Application No. 62/621,299, filed Jan. 24, 2018; and Provisional Application No. 62/501,390, filed May 4, 2017; the disclosure of each of which is incorporated herein by reference in its entirety.

TECHNICAL FIELD OF THE INVENTION

The present invention relates to compositions for treating eyes, methods for treating eyes, and methods for preparing said compositions and more specifically to treating the eyes for glaucoma, for post-op care after various eye surgeries, and/or for dry eyes.

COPYRIGHT AND TRADEMARK NOTICE

A portion of the disclosure of this patent application may contain material that is subject to copyright protection. The owner has no objection to the facsimile reproduction by anyone of the patent document or the patent disclosure, as it appears in the Patent and Trademark Office patent file or records, but otherwise reserves all copyrights whatsoever.

Certain marks referenced herein may be common law or registered trademarks of third parties affiliated or unaffiliated with the applicant or the assignee. Use of these marks is by way of example and should not be construed as descriptive or to limit the scope of this invention to material associated only with such marks.

BACKGROUND OF THE INVENTION

Today (circa 2018) many people face various problems with their eyes, such as glaucoma, preparation for eye surgery, care during eye surgery, necessary post-op care after various eye surgeries (e.g., after cataract surgery, Lasik surgery, Lasik like surgery, laser surgery, and the like), dry eyes, and the like. Typical treatments for such eye problems include treatments, via eye drops and/or intra-cameral injections, of a variety of different packaged medications, typically each with one given API (active pharmaceutical ingredient), which may result in patient compliance problems because the patient needs to use multiple eye droppers for a given dosing (or multiple injections for a given dosing), and increased patient cost problems.

It would be desirable if such different packaged medications could be formulated to exist in a single package or delivery device, which may be improve patient compliance and reduce costs to the patient. Dosing from a single container (that combines APIs) as opposed to multiple containers where the APIs are in separate and different containers, also exposes the patient to fewer preservatives. It would also be desirable if such a combined single packaging or delivery device, also increased efficacy and/or minimized side-effects.

It is to these ends that the present invention has been developed.

BRIEF SUMMARY OF THE INVENTION

To minimize the limitations in the prior art, and to minimize other limitations that will be apparent upon reading and understanding the present specification, embodiments of the present invention may describe pharmaceutical compositions, methods for treating various issues of the eyes, and methods of preparing such compositions are described. These pharmaceutical compositions may be for treating glaucoma, various post-op care (e.g., after cataract surgery, laser eye surgery, and the like), and/or for treating dry eyes. These pharmaceutical compositions may comprise such active ingredients (APIs) as: timolol, latanoprost, brimonidine tartrate, dorzolamide, moxifloxacin HCl, dexamethasone PO4, ketorolac tromethamine, phenylephrine HCl, lidocaine HCl, bromfenac, prednisolone PO4, gatifloxacin, amniotic cytokine extract (ACE), prostaglandin E2 (PGE2), and combinations thereof.

It is an objective of the present invention to provide pharmaceutical compositions and/or methods of treating eyes with given pharmaceutical compositions.

It is another objective of the present invention to provide pharmaceutical compositions and/or methods of treating eyes with given pharmaceutical compositions that result in increased patient compliance, e.g., by minimizing the number of treatments or by minimizing the number of separate medications being used.

It is another objective of the present invention to provide pharmaceutical compositions and/or methods of treating eyes with given pharmaceutical compositions that result in improved efficacy.

It is another objective of the present invention to provide pharmaceutical compositions and/or methods of treating eyes with given pharmaceutical compositions that result in minimal side-effects.

It is yet another objective of the present invention to provide pharmaceutical compositions and/or methods of treating eyes with given pharmaceutical compositions that result in minimal or better cost savings for the patient, e.g., by minimizing the number of separate medications which must be administered to the eyes.

These and other advantages and features of the present invention are described herein with specificity so as to make the present invention understandable to one of ordinary skill in the art, both with respect to how to practice the present invention and how to make the present invention.

BRIEF DESCRIPTION OF THE SEVERAL VIEWS OF THE DRAWINGS

Elements in the figures have not necessarily been drawn to scale in order to enhance their clarity and improve understanding of these various elements and embodiments of the invention. Furthermore, elements that are known to be common and well understood to those in the industry are not depicted in order to provide a clear view of the various embodiments of the invention.

FIG. 3 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 3 may depict some baseline characteristics.

FIG. 6 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 6 may depict morning IOP change from baseline.

FIG. 9 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 9 may depict visual acuity change from baseline.

FIG. 10 may depict a table from a study on a pharmaceutical composition comprising prednisolone PO4 (phosphate) 1% and gatifloxacin 0.5%; wherein FIG. 10 may depict UCDVA (uncorrected distance visual acuity) frequencies.

FIG. 11 may depict a table from a study on a pharmaceutical composition comprising prednisolone PO4 (phosphate) 1% and gatifloxacin 0.5%; wherein FIG. 11 may depict UCDVA (uncorrected distance visual acuity) frequencies.

FIG. 12 may depict a table from a study on a pharmaceutical composition comprising prednisolone PO4 (phosphate) 1% and gatifloxacin 0.5%; wherein FIG. 12 may depict UCVA (uncorrected visual acuity) outcomes summary.

FIG. 13 may depict a table from a study on a pharmaceutical composition comprising prednisolone PO4 (phosphate) 1% and gatifloxacin 0.5%; wherein FIG. 13 may depict AC Cell results.

FIG. 14 may depict a table from a study on a pharmaceutical composition comprising prednisolone PO4 (phosphate) 1% and gatifloxacin 0.5%; wherein FIG. 14 may depict AC flare results.

FIG. 15 may depict a table from a study on a pharmaceutical composition comprising prednisolone PO4 (phosphate) 1% and gatifloxacin 0.5%; wherein FIG. 15 may depict total corneal staining (TCS) results.

FIG. 16 may depict a table from a study on a pharmaceutical composition comprising prednisolone PO4 (phosphate) 1% and gatifloxacin 0.5%; wherein FIG. 16 may depict IOP (intraocular pressure) change from baseline.

FIG. 17 may depict a table from a study on a pharmaceutical composition comprising PGE2 and active cytokines from amniotic cytokine extract; wherein FIG. 17 may depict summary of week 4 study results.

FIG. 18 may depict a table from a study on a pharmaceutical composition comprising PGE2 and active cytokines from amniotic cytokine extract; wherein FIG. 18 may depict summary of week 12 study results.

DETAILED DESCRIPTION OF THE INVENTION

Figure 1:
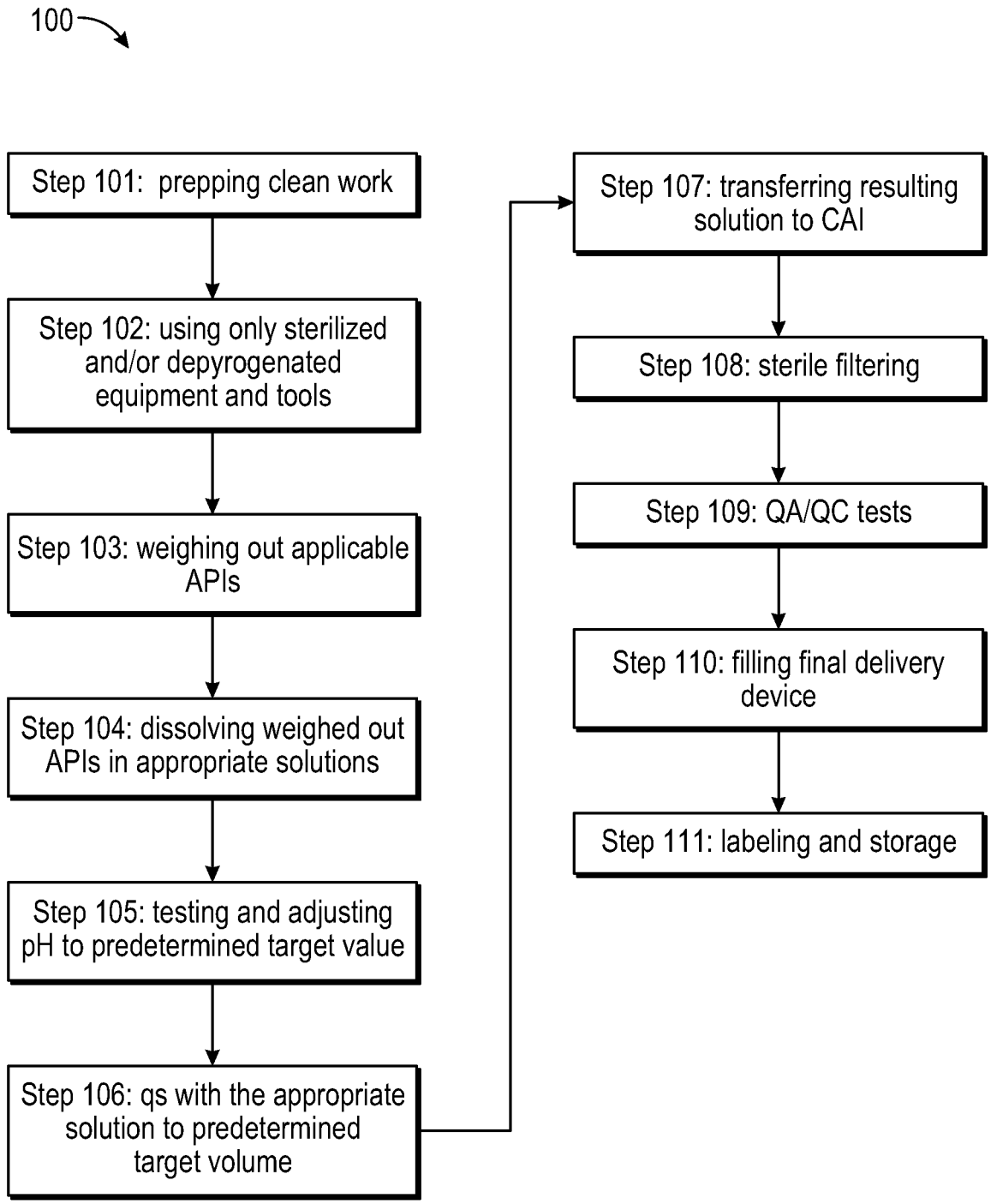
FIG. 1 may depict a flow diagram of a method; wherein this method may comprise steps for compounding and/or filling a given pharmaceutical composition.

Below is a table listing at least fifteen separate and distinct pharmaceutical compositions by their respective APIs (active pharmaceutical ingredients), as well as listing at least one treatment purpose and at least one delivery device or method that may be contemplated embodiments of the present invention:

| | Compositions of APIs | Sample Treatment Purpose | Sample Delivery Device/Method |
|---|---|---|---|
| 1 | Timolol 0.5%, Latanoprost 0.005% | for treating glaucoma | eye drops |
| 2 | Timolol 0.5%, Brimonidine Tartrate 0.2%, Dorzolamide 2% | for treating glaucoma | eye drops |
| 3 | Timolol 0.5%, Brimonidine Tartrate 0.2%, | for treating glaucoma | eye drops |

| | Compositions of APIs | Sample Treatment Purpose | Sample Delivery Device/Method |
|---|---|---|---|
| | Dorzolamide 2%, Latanoprost 0.005% | | |
| 4 | Moxifloxacin HCl 0.5% | post-op care after cataract surgery | intra-cameral injection |
| 5 | Dexamethasone PO4 0.1%, Moxifloxacin HCl 0.5% | post-op care after cataract surgery | intra-cameral injection |
| 6 | Dexamethasone PO4 0.1%, Moxifloxacin HCl 0.5%, Ketorolac Tromethamine 0.5% | post-op care after cataract surgery | intra-cameral injection |
| 7 | Dexamethasone PO4 0.1%, Moxifloxacin HCl 0.5%, Bromfenac 0.07% | post-op care after cataract surgery | intra-cameral injection |
| 8 | Prednisolone PO4 1%, Gatifloxacin 0.5% | post-op care after Lasik surgery | eye drops |
| 9 | Prednisolone PO4 1%, Ketorolac Tromethamine 0.5% | post-op care for retina after surgery | eye drops |
| 10 | Prednisolone PO4 1%, Ketorolac Tromethamine 0.5%, Gatifloxacin 0.5% | post-op care after cataract surgery | eye drops |
| 11 | Prednisolone PO4 1%, Bromfenac 0.07% | post-op care for retina after surgery | eye drops |
| 12 | Prednisolone PO4 1%, Gatifloxacin 0.5%, Bromfenac 0.07% | post-op care after cataract surgery | eye drops |
| 13 | Prostaglandin E2 (PGE2) | for treating dry eyes | eye drops |
| 14 | Phenylephrine HCl 1.5%, Lidocaine HCl 1%, Ketorolac Tromethamine 0.3% | pre-op or during cataract surgery | intra-cameral injection |
| 15 | Phenylephrine HCl 1.5%, Lidocaine HCl 1%, Bromfenac 0.01% | pre-op or during cataract surgery | intra-cameral injection |

HCl in the above formulations may be a standard chemical abbreviation for hydrochloride or hydrochloric acid. PO4 in the above formulations may be a standard chemical abbreviation for phosphate.

Each of the above of the at least fifteen pharmaceutical compositions are discussed further and in more detail below.

Discussion of Timolol 0.5%, Latanoprost 0.005%

In some embodiments, a pharmaceutical composition may comprise at least two active ingredients (APIs), timolol maleate (timolol) and latanoprost.

In some embodiments, timolol maleate may also be known as timolol, timolol hemihydrate, and timolol ophthalmic solution. In some embodiments, timolol maleate may be a non-selective beta-adrenergic receptor blocking agent. Mechanism of action may be through blockage of both beta1 and beta2-adrenergic receptors and reduction of intraocular pressure by reducing aqueous humor production or increasing outflow of aqueous humor. In some embodiments, timolol maleate may work to decrease fluid production and pressure inside the eye. In some embodiments, timolol maleate may be used for treating increased pressure in the eye (ocular hypertension) and/or glaucoma (e.g., open-angle glaucoma). In some embodiments, timolol maleate may be indicated for the treatment of elevated intraocular pressure (IOP) in patients with ocular hypertension and/or open-angle glaucoma.

In some embodiments, the timolol may be present in the pharmaceutical composition at 0.5%; that is each mL (milliliter) of the pharmaceutical composition may contain 5 mg (milligram) of timolol (6.8 mg of timolol maleate).

In some embodiments, latanoprost may be known as latanoprost ophthalmic solution. In some embodiments, latanoprost may be in the prostaglandin analogue family of medication; i.e., a prostaglandin analog. Mechanism of action may be through a prostaglandin F2-alpha analog to reduce intraocular pressure by increasing the outflow of the aqueous humor. In some embodiments, the latanoprost may work by increasing the outflow of aqueous fluid from the eyes through the uveoscleral tract. In some embodiments, latanoprost may be indicated for the treatment of elevated intraocular pressure (IOP) in patients with open-angle glaucoma and/or ocular hypertension. In some embodiments, the latanoprost may be used for treating increased pressure in the eye (ocular hypertension) and glaucoma (e.g., open-angle glaucoma). In some embodiments, the latanoprost may be present in the pharmaceutical composition at 0.005%; that is each mL of pharmaceutical composition may contain 50 mcg (microgram) of latanoprost.

In some embodiments, this pharmaceutical composition may also comprise sodium chloride (NaCl) for purposes of yielding an isotonic, buffered, aqueous solution.

In some embodiments, this pharmaceutical composition may also comprise sodium chloride and/or sodium hydroxide (NaOH) for purposes of adjusting pH of the resulting pharmaceutical composition to a target pH of 6.7. In some embodiments, this pharmaceutical composition may also comprise hydrochloric acid (HCl) for pH adjustment purposes.

In some embodiments, this pharmaceutical composition may comprise benzalkonium chloride (BAK), in addition to the timolol maleate and the latanoprost. In some embodiments, BAK may be a detergent, a quaternary ammonium compound with a broad range of antimicrobial activity. In some embodiments, BAK may be a preservative in the pharmaceutical composition.

In some embodiments, a carrier and/or a solvent of the timolol 0.5% and the latanoprost 0.005% pharmaceutical composition may be water. In some embodiments, this water may be sterile water, water for irrigation, water for injection (WFI), or the like.

In some embodiments, the timolol 0.5% and the latanoprost 0.005% pharmaceutical composition may be delivered to the eyes of a patient via use eye drops from an eye dropper.

In some embodiments, the timolol 0.5% and the latanoprost 0.005% pharmaceutical composition may be used for treating glaucoma in the eye(s).

In some embodiments, compounding the pharmaceutical composition comprising the timolol 0.5% and the latanoprost 0.005% may comprise steps of: (step 101) prepping clean work area (e.g., cleaning and/or disinfecting); (step 102) using only sterilized and/or depyrogenated equipment;

(step 103) weighing applicable APIs (e.g., timolol maleate and latanoprost) in a powder hood (with the 0.5% and the 0.005% targets in mind); (step 104) dissolving weighed out API powders in sterile water (or WFI) (with the 0.5% and the 0.005% targets in mind); (step 105) testing and adjusting the pH to a target of 6.7 via use of sodium chloride, sodium hydroxide, and pH meter (calibrated); (step 106) qs ("quantity sufficient") with the sterile water (or WFI) with the 0.5% and 0.005% targets in mind; (step 107) transferring resulting solution to a compounding aseptic isolator (CAI); (step 108) sterile filtering (e.g., a 0.22 micron filter) the resulting solution to yield the pharmaceutical composition comprising the timolol 0.5% and the latanoprost 0.005%; (step 109) QA/QC (quality assurance/quality control) tests, such as bubble point testing, sterility testing, and/or endotoxin testing; (step 110) and filling final delivery device, e.g., a sterile ophthalmic dropper bottle (e.g., a "drop-tainer," "steridropper," or the like); and (step 111) of label and storage. See e.g., FIG. 1. In some embodiments, the final delivery device, e.g., the sterile ophthalmic dropper bottle, may be light resistant.

For example, and without limiting the scope of the present invention, a 200 mL batch of the pharmaceutical composition comprising the timolol 0.5% and the latanoprost 0.005% may comprise: 1.360 grams of timolol maleate; 1.030 grams of latanoprost stock solution (at 10 mg/g); 1.600 grams of sodium chloride; 2.000 mL of BAK 1%; and the balance of sterile water (or WFI).

In some embodiments, the pharmaceutical composition may comprise timolol 0.5%, latanoprost 0.005%, sodium chloride, BAK, sodium hydroxide, and water; wherein that pharmaceutical composition may have a pH of 6.7.

Discussion of Timolol 0.5%, Brimonidine Tartrate 0.2%, Dorzolamide 2%

In some embodiments, a pharmaceutical composition may comprise at least three active ingredients (APIs), timolol maleate (timolol), brimonidine tartrate, and dorzolamide.

In some embodiments, the timolol may be as discussed above.

In some embodiments, brimonidine tartrate may also be known as brimonidine and brimonidine ophthalmic solution. Mechanism of action may be through relative selective alpha-2 adrenergic agonist causing reduction of aqueous humor formation and increased uveoscleral outflow. In some embodiments, the brimonidine tartrate may be a relatively selective alpha-2 adrenergic agonist. In some embodiments, the brimonidine tartrate may function via a dual mechanism of action by reducing aqueous humor production and increasing uveoscleral outflow. In some embodiments, brimonidine tartrate may be indicated for the treatment of elevated intraocular pressure (IOP) in patients with open-angle glaucoma and/or ocular hypertension. In some embodiments, the brimonidine tartrate may be used for treating increased pressure in the eye (ocular hypertension) and glaucoma (e.g., open-angle glaucoma). In some embodiments, the brimonidine tartrate may be present in the pharmaceutical composition at 0.2%; that is each mL of the pharmaceutical composition may contain 2 mg of brimonidine tartrate.

In some embodiments, the dorzolamide may be known as dorzolamide ophthalmic solution. Mechanism of action may be through reversible inhibition of the enzyme carbonic anhydrase resulting in reduction of hydrogen ion secretion at the renal tubule and an increased renal excretion of sodium, potassium, bicarbonate, and water to decrease production of aqueous humor. Dorzolamide may also inhibit carbonic anhydrase in the central nervous system (CNS) to retard abnormal and excessive discharge from CNS neurons. In some embodiments, the dorzolamide may be a carbonic anhydrase inhibitor. In some embodiments, the dorzolamide may work by decreasing fluid production and pressure inside the eye. In some embodiments, the dorzolamide may be indicated for the treatment of elevated intraocular pressure (IOP) in patients with ocular hypertension and/or open-angle glaucoma. In some embodiments, the dorzolamide may be used for treating increased pressure in the eye (ocular hypertension) and/or glaucoma (e.g., open-angle glaucoma). In some embodiments, the dorzolamide may be present in the pharmaceutical composition as dorzolamide HCl. In some embodiments, the dorzolamide may be present in the pharmaceutical composition at 2%; that is, each mL of the pharmaceutical composition may contain 20 mg of dorzolamide (e.g., 22.26 mg of dorzolamide HCl).

In some embodiments, this pharmaceutical composition may also comprise sodium phosphate monobasic.

In some embodiments, this pharmaceutical composition may also comprise sodium phosphate monobasic and/or sodium hydroxide for purposes of adjusting pH of the resulting pharmaceutical composition to a target pH of 5.8.

In some embodiments, this pharmaceutical composition may comprise BAK, in addition to the timolol maleate, the brimonadine tartrate, and the dorzolamide. In some embodiments, BAK may be a detergent, a quaternary ammonium compound with a broad range of antimicrobial activity. In some embodiments, BAK may be a preservative in the pharmaceutical composition.

In some embodiments, a carrier and/or a solvent of the timolol 0.5%, brimonidine tartrate 0.2%, and dorzolamide 2% pharmaceutical composition may be water. In some embodiments, this water may be sterile water, water for irrigation, water for injection (WFI), or the like.

In some embodiments, the timolol 0.5%, brimonidine tartrate 0.2%, and dorzolamide 2% pharmaceutical composition may be delivered to the eyes of a patient via use eye drops from an eye dropper.

In some embodiments, the timolol 0.5%, brimonidine tartrate 0.2%, and dorzolamide 2% pharmaceutical composition may be used for treating glaucoma in the eye(s).

In some embodiments, compounding the pharmaceutical composition comprising the the timolol 0.5%, brimonidine tartrate 0.2%, and dorzolamide 2% may comprise steps of: (step 101) prepping clean work area (e.g., cleaning and/or disinfecting); (step 102) using only sterilized and/or depyrogenated equipment; (step 103) weighing applicable APIs (e.g., timolol maleate, brimonadine tartrate, and dorzolamide) in a powder hood (with the 0.5%, 0.2%, and 2% targets in mind, respectively); (step 104) dissolving weighed out API powders in sterile water (or WFI) (with the 0.5%, 0.2%, and 2% targets in mind, respectively); (step 105) testing and adjusting the pH to a target of 5.8 via use of sodium phosphate monobasic, sodium hydroxide, and pH meter (calibrated); (step 106) qs ("quantity sufficient") with the sterile water (or WFI) with the 0.5%, 0.2%, and 2% targets in mind, respectively; (step 107) transferring resulting solution to CAI; (step 108) sterile filtering (e.g., using 0.22 micron filter) the resulting solution to yield the pharmaceutical composition comprising the timolol 0.5%, brimonidine tartrate 0.2%, and dorzolamide 2%; (step 109) QA/QC tests, such as bubble point testing, sterility testing, and/or endotoxin testing; (step 110) filling final delivery device, e.g., a sterile ophthalmic dropper bottle (e.g., a "drop-tainer," "steri-dropper," or the like); and (step 111)

labeling and storage. See e.g., FIG. 1. In some embodiments, the final delivery device, e.g., the sterile ophthalmic dropper bottle, may be light resistant.

For example, and without limiting the scope of the present invention, a 100 mL batch of the pharmaceutical composition comprising the timolol 0.5%, brimonidine tartrate 0.2%, and dorzolamide 2% may comprise: 0.68 grams of timolol maleate; 0.2 grams of brimonadine tartrate; 2.225 grams of dorzolamide HCl; 0.86 grams of sodium phosphate monobasic; 1.00 mL of BAK; and the balance of sterile water for irrigation (or WFI).

In some embodiments, the pharmaceutical composition may comprise timolol 0.5%, brimonidine tartrate 0.2%, dorzolamide 2%, sodium phosphate, BAK, sodium hydroxide, and water; wherein that pharmaceutical composition may have a pH of 5.8.

Discussion of Timolol 0.5%, Brimonidine Tartrate 0.2%, Dorzolamide 2%, and Latanoprost 0.005%

In some embodiments, a pharmaceutical composition may comprise at least four active ingredients (APIs), timolol maleate (timolol), brimonidine tartrate, dorzolamide, and latanoprost.

In some embodiments, the timolol may be as discussed above.

In some embodiments, the brimonidine tartrate may be as discussed above.

In some embodiments, the dorzolamide may be as discussed above.

In some embodiments, the latanoprost may be as discussed above.

In some embodiments, this pharmaceutical composition may also comprise sodium chloride for purposes of yielding an isotonic, buffered, aqueous solution.

In some embodiments, this pharmaceutical composition may also comprise sodium chloride and/or sodium hydroxide (NaOH) for purposes of adjusting pH of the resulting pharmaceutical composition to a target pH of 5.8 to 5.9). In some embodiments, HCl may also have been used to adjust pH.

In some embodiments, this pharmaceutical composition may comprise BAK, in addition to the timolol maleate, the brimonidine tartrate, the dorzolamide, and the latanoprost. In some embodiments, BAK may be a detergent, a quaternary ammonium compound with a broad range of antimicrobial activity. In some embodiments, BAK may be a preservative in the pharmaceutical composition.

In some embodiments, a carrier and/or a solvent of the timolol 0.5%, brimonidine tartrate 0.2%, dorzolamide 2%, and latanoprost 0.005% pharmaceutical composition may be water. In some embodiments, this water may be sterile water, water for irrigation, water for injection (WFI), or the like.

In some embodiments, the timolol 0.5%, brimonidine tartrate 0.2%, dorzolamide 2%, and latanoprost 0.005% pharmaceutical composition may be delivered to the eyes of a patient via use eye drops from an eye dropper. In some embodiments, a 10 mL ophthalmic dropper bottle may be used to receive a fill volume of 3.5 mL of this prepared pharmaceutical composition.

In some embodiments, the timolol 0.5%, brimonidine tartrate 0.2%, dorzolamide 2%, and latanoprost 0.005% pharmaceutical composition may be used for treating glaucoma in the eye(s).

In some embodiments, compounding the pharmaceutical composition comprising the the timolol 0.5%, brimonidine tartrate 0.2%, dorzolamide 2%, and latanoprost 0.005% may comprise steps of: (step 101) prepping clean work area (e.g., cleaning and/or disinfecting); (step 102) using only sterilized and/or depyrogenated equipment; (step 103) weighing applicable APIs (e.g., timolol maleate, brimonadine tartrate, dorzolamide, and latanoprost) in a powder hood (with the 0.5%, 0.2%, 2%, and 0.005% targets in mind, respectively); (step 104) dissolving weighed out API powders in sterile water (or WFI) (with the 0.5%, 0.2%, 2%, and 0.005% targets in mind, respectively); (step 105) testing and adjusting the pH to a target of 5.8 (of pH 5.8 to 5.9) via use of sodium hydroxide, and pH meter (calibrated); (step 106) qs ("quantity sufficient") with the sterile water (or WFI) with the 0.5%, 0.2%, 2%, and 0.005% targets in mind, respectively; (step 107) transferring resulting solution to CAI; (step 108) sterile filtering (e.g., using 0.22 micron filter) the resulting solution to yield the pharmaceutical composition comprising the timolol 0.5%, brimonidine tartrate 0.2%, dorzolamide 2%, and latanoprost 0.005%; (step 109) QA/QC tests, such as, clarity, appearance, bubble point testing, sterility testing, and/or endotoxin testing; (step 110) filling final delivery device, e.g., a sterile ophthalmic dropper bottle (e.g., a "drop-tainer," "steri-dropper," or the like); and (step 111) labeling and storage. See e.g., FIG. 1. In some embodiments, the final delivery device, e.g., the sterile ophthalmic dropper bottle, may be light resistant.

For example, and without limiting the scope of the present invention, a 100 mL batch of the pharmaceutical composition comprising the timolol 0.5%, brimonidine tartrate 0.2%, dorzolamide 2%, and latanoprost 0.005% may comprise: 0.68 grams of timolol maleate; 0.2 grams of brimonidine tartrate; 2.225 grams of dorzolamide HCl; 0.515 grams of latanoprost stock (at 10 mg/g); 0.42 grams of sodium chloride; 1.00 mL of BAK 1%; and the balance of sterile water (or WFI).

In some embodiments, it may be important not to exceed a pH of 6 with this pharmaceutical composition, as higher pH's may cause undesired precipitation.

In some embodiments, the pharmaceutical composition may comprise timolol 0.5%, brimonidine tartrate 0.2%, dorzolamide 2%, latanoprost 0.005%, sodium chloride, BAK, sodium hydroxide, and water; wherein that pharmaceutical composition may have a pH of 5.8 (or a pH of 5.8 to 5.9). In some embodiments, this pharmaceutical composition may have a beyond-use date of at least 180 days. This pharmaceutical composition may be stored refrigerated. In some embodiments, this pharmaceutical composition may be slightly opaque and slightly yellowish in appearance.

In some embodiments, this pharmaceutical composition with the at least three active ingredients (APIs), may have increased efficacy, improved drug delivery, better patient compliance, and have cost savings for patients (e.g., purchasing less medication containers/delivery devices), as compared against pharmaceutical compositions with only one or two active ingredients (APIs).

Discussion of Moxifloxacin HCL 0.5%

In some embodiments, a pharmaceutical composition may comprise at least one active ingredient (API), moxifloxacin HCl. In some embodiments, this pharmaceutical composition may comprise moxifloxacin HCl at 0.5% (weight per volume). In some embodiments, this pharmaceutical composition may be preservative free; which may result in increased efficacy as compared to pharmaceutical compositions with preservatives.

In some embodiments, moxifloxacin HCl may be known as moxifloxacin or moxifloxacin hydrochloride. In some embodiments, moxifloxacin HCl may be a synthetic fluoroquinolone antibacterial agent. In some embodiments, moxifloxacin may be used in an ophthalmic solution. In some embodiments, moxifloxacin may be used for the treatment of bacterial conjunctivitis (i.e., pink eye). Mechanism of action of moxifloxacin HCl may be through inhibition of DNA gyrase and topoisomerase IV which may be required for some bacterial DNA replication, transcription, repair, and/or recombination.

In some embodiments, the moxifloxacin HCl may be present in the pharmaceutical composition at 0.5%; that is, each mL of the pharmaceutical composition may contain 5 mg of moxifloxacin HCl.

In some embodiments, this pharmaceutical composition may also comprise sodium chloride for purposes of yielding an isotonic, buffered, aqueous solution.

In some embodiments, this pharmaceutical composition may also comprise sodium chloride, sodium hydroxide, and/or hydrochloric acid (HCl) for purposes of adjusting pH of the resulting pharmaceutical composition to a final target pH of 7.2.

In some embodiments, a carrier and/or a solvent of the moxifloxacin HCl 0.5% pharmaceutical composition may be water. In some embodiments, this water may be sterile water, water for injection (WFI), or the like.

In some embodiments, the moxifloxacin HCl 0.5% pharmaceutical composition may be delivered to the eyes of a patient via use of an injection, as in an intra-cameral injection.

In some embodiments, the moxifloxacin HCl 0.5% pharmaceutical composition may be used for post-op care of an eye after cataract surgery of that eye. Such use of the moxifloxacin HCl 0.5%, post-op, may minimize post-op infections; and/or may improve recovery from the cataract surgery, both in terms of speed of recovery quality of vision improvement.

In some embodiments, compounding the pharmaceutical composition comprising the the moxifloxacin HCl 0.5% may comprise steps of: (step 101) prepping clean work area (e.g., cleaning and/or disinfecting); (step 102) using only sterilized and/or depyrogenated equipment; (step 103) weighing applicable API (e.g., moxifloxacin HCl) in a powder hood (with the 0.5% target in mind); (step 104) dissolving weighed out API powder in sterile water (or WFI) (with the 0.5% target in mind); (step 105) testing and adjusting the pH to a final target of 7.2 via use of HCl, sodium hydroxide, sodium chloride, and a pH meter (calibrated); (step 106) qs ("quantity sufficient") with the sterile water (or WFI) with the 0.5% target in mind; (step 107) transferring resulting solution to a CAI; (step 108) sterile filtering (e.g., using a 0.22 micron filter) the resulting solution to yield the pharmaceutical composition comprising the moxifloxacin HCl 0.5%; (step 109) QA/QC tests, such as bubble point testing, sterility testing, and/or endotoxin testing; (step 110) filling final container, e.g., a sterile vial; and (step 111) labeling and storage. See e.g., FIG. 1. In some embodiments, step 104 of dissolving weighed out API powder in sterile water (or WFI), i.e., of dissolving moxifloxacin HCl powder into water, may be facilitated by adding some HCl (e.g., adding 5 mL of HCl 0.1 N per a 100 mL batch) and stirring for about 20 minutes, at room temperature. In some embodiments, a 2 mL sterile vial may be used as the final container. In some embodiments, a 2 mL sterile vial may be filled to 1 mL with the pharmaceutical composition.

For example, and without limiting the scope of the present invention, a 100 mL batch of the pharmaceutical composition comprising the moxifloxacin HCl 0.5% may comprise: 0.523 grams of moxifloxacin HCl; 0.812 grams of sodium chloride; and the balance of sterile water (or WFI); with negligible amounts of HCl and/or sodium hydroxide for pH adjustments to a final target value of 7.2.

Discussion of Dexamethasone PO4 0.1%, Moxifloxacin HCL 0.5%

In some embodiments, a pharmaceutical composition may comprise at least two active ingredients (APIs), dexamethasone PO4 (phosphate) and moxifloxacin HCl.

In some embodiments, dexamethasone may be known as dexamethasone PO4, dexamethasone phosphate, dexamethasone sodium PO4, dexamethasone sodium phosphate, dexamethasone NaPO4. In some embodiments, dexamethasone PO4 may be a type of corticosteroid. In some embodiments, dexamethasone PO4 may be a synthetic glucocorticoid. In some embodiments, dexamethasone PO4 may be indicated for treatment of inflammation. In some embodiments, dexamethasone may have anti-inflammatory and immunosuppressant effects. In some embodiments, the anti-inflammatory properties of dexamethasone may be useful in post-op care of an eye following cataract surgery of that eye. Mechanism of action of dexamethasone PO4 may involve inhibition of phospholipase A2, inhibitory proteins, and/or lipocortins which modulate prostaglandins and leukotrienes.

In some embodiments, the dexamethasone PO4 may be present in the pharmaceutical composition at 0.1%; that is, each mL of the pharmaceutical composition may contain 1 mg of the dexamethasone PO4.

In some embodiments, the moxifloxacin HCl may be as discussed above.

In some embodiments, this pharmaceutical composition may also comprise sodium chloride (NaCl) for purposes of yielding an isotonic, buffered, aqueous solution.

In some embodiments, this pharmaceutical composition may also comprise sodium chloride, sodium hydroxide (NaOH), and/or hydrochloric acid (HCl) for purposes of adjusting pH of the resulting pharmaceutical composition to a final target pH of 7 to 7.2.

In some embodiments, a carrier and/or a solvent of the dexamethasone PO4 0.1%, moxifloxacin HCl 0.5% pharmaceutical composition may be water. In some embodiments, this water may be sterile water, water for injection (WFI), or the like.

In some embodiments, the dexamethasone PO4 0.1%, moxifloxacin HCl 0.5% pharmaceutical composition may be delivered to the eyes of a patient via use of an injection, as in an intra-cameral injection. In some embodiments, a sterile and/or depyrogenated 2 mL glass vial may receive a fill volume of 1 mL of this pharmaceutical composition.

In some embodiments, the dexamethasone PO4 0.1%, moxifloxacin HCl 0.5% pharmaceutical composition may be used for post-op care of an eye after cataract surgery of that eye. Such use of the dexamethasone PO4 0.1%, moxifloxacin HCl 0.5%, post-op, may minimize post-op infections; and/or may improve recovery from the cataract surgery, both in terms of speed of recovery quality of vision improvement.

In some embodiments, compounding the pharmaceutical composition comprising the dexamethasone PO4 0.1%, the moxifloxacin HCl 0.5% may comprise steps of: (step 101) prepping clean work area (e.g., cleaning and/or disinfecting); (step 102) using only sterilized and/or depyrogenated equipment; (step 103) weighing applicable APIs (e.g., the dexamethasone NaPO4 and the moxifloxacin HCl) in a powder hood (with the 0.1% and the 0.5% targets in mind); (step 104) dissolving the weighed out API powders in sterile water (or WFI) (with the 0.1% and the 0.5% targets in mind); (step 105) testing and adjusting the pH to a final target of 7.2 via use of HCl, sodium hydroxide, sodium chloride, and a pH meter (calibrated); (step 106) qs ("quantity sufficient")

with the sterile water (or WFI) with the 0.1% and the 0.5% targets in mind; (step 107) transferring resulting solution to a CAI; (step 108) sterile filtering (e.g., using a 0.22 micron filter) the resulting solution to yield the pharmaceutical composition comprising the dexamethasone PO4 0.1%, moxifloxacin HCl 0.5%; (step 109) QA/QC tests, such as bubble point testing, sterility testing, and/or endotoxin testing; (step 110) filling final container, e.g., a sterile vial; and (step 111) labeling and storage. In some embodiments, step 104 of dissolving weighed out API powders in sterile water (or WFI), i.e., of dissolving the moxifloxacin HCl powder into the water, may be facilitated by adding some HCl (e.g., adding 5 mL of HCl 0.1 N per a 100 mL batch) and stirring for about 20 minutes, at room temperature. Which in some embodiments, may then be followed by adjusting the pH to 6.9 using about 20 mL of sodium hydroxide 1%; and then adding in the sodium chloride and dexamethasone sodium phosphate; and then proceeding with step 105 of adjusting the final pH to 7.2. In some embodiments, a 2 mL sterile vial may be used as the final container. In some embodiments, a 2 mL sterile (and/or depyrogenated) vial may be filled to 1 mL with the pharmaceutical composition.

For example, and without limiting the scope of the present invention, a 100 mL batch of the pharmaceutical composition comprising the dexamethasone PO4 0.1%, moxifloxacin HCl 0.5% may comprise: 0.523 grams of moxifloxacin HCl; 0.114 grams of dexamethasone sodium PO4; 0.812 grams of sodium chloride; and the balance of sterile water (or WFI); with negligible amounts of HCl and/or sodium hydroxide for pH adjustments to a final target value of 7.2.

In some embodiments, the pharmaceutical composition may comprise dexamethasone PO4 0.1%, moxifloxacin HCl 0.5%, sodium chloride, hydrochloric acid, sodium hydroxide, and water; wherein that pharmaceutical composition may have a pH of 7 to 7.2. In some embodiments, this pharmaceutical composition may be preservative free; which may result in increased efficacy as compared to pharmaceutical compositions with preservatives. In some embodiments, this pharmaceutical composition may have a beyond-use date of at least 180 days. Storage may be room temperature. In some embodiments, this pharmaceutical composition may be clear and yellowish in appearance.

In some embodiments, this pharmaceutical composition with dexamethasone PO4 0.1% and moxifloxacin HCl 0.5% may improve patient compliance by reducing a number treatments.

Discussion of Dexamethasone PO4 0.1%, Moxifloxacin HCL 0.5%, Ketorolac Tromethamine 0.5%

In some embodiments, a pharmaceutical composition may comprise at least three active ingredients (APIs), dexamethasone PO4, moxifloxacin HCl, and ketorolac tromethamine.

In some embodiments, the dexamethasone may be as discussed above.

In some embodiments, the moxifloxacin HCl may be as discussed above.

In some embodiments, the ketorolac tromethamine may also be known as ketorolac, ketorolac tromethamine ophthalmic solution, and ketorolac tromethamine injection. In some embodiments, the ketorolac tromethamine may be a non-steroidal anti-inflammatory drug (NSAID), in the family of heterocyclic acetic acid derivatives. In some embodiments, the ketorolac tromethamine may be used as an analgesic. In some embodiments, ketorolac tromethamine may be used to treat inflammation in the eye, at the eye, and/or around the eye. In some embodiments, ketorolac tromethamine may be sued to treat eye inflammation post eye surgery. In some embodiments, ketorolac tromethamine may be used to during eye surgery, during an intraocular ophthalmic procedure, and/or before an intraocular procedure in preparation for that procedure. In some embodiments, the pharmaceutical composition containing ketorolac tromethamine may have a pH of 7.2 to 7.8. Mechanism of action for K may be through inhibition of prostaglandin synthesis secondary to inhibition of COX (cyclooxygenase) production; wherein COX inhibition may be nonselective.

In some embodiments, the ketorolac tromethamine may be present in the pharmaceutical composition at 0.5%; that is, each mL of the pharmaceutical composition may contain 5 mg of the ketorolac tromethamine.

In some embodiments, this pharmaceutical composition may also comprise sodium chloride for purposes of yielding an isotonic, buffered, aqueous solution.

In some embodiments, this pharmaceutical composition may also comprise sodium chloride, sodium hydroxide, and/or hydrochloric acid (HCl) for purposes of adjusting pH of the resulting pharmaceutical composition to a final target pH of 7.0 to 7.2.

In some embodiments, a carrier and/or a solvent of the dexamethasone PO4 0.1%, moxifloxacin HCl 0.5%, ketorolac tromethamine 0.5% pharmaceutical composition may be water. In some embodiments, this water may be, sterile water for injection (WFI).

In some embodiments, the dexamethasone PO4 0.1%, moxifloxacin HCl 0.5%, ketorolac tromethamine 0.5% pharmaceutical composition may be delivered to the eyes of a patient via use of an injection, as in an intra-cameral injection.

In some embodiments, the dexamethasone PO4 0.1%, moxifloxacin HCl 0.5%, ketorolac tromethamine 0.5% pharmaceutical composition may be used for post-op care of an eye after cataract surgery of that eye. Such use of the dexamethasone PO4 0.1%, moxifloxacin HCl 0.5%, ketorolac tromethamine 0.5%, post-op, may minimize post-op infections; and/or may improve recovery from the cataract surgery, both in terms of speed of recovery quality of vision improvement.

In some embodiments, compounding the pharmaceutical composition comprising the dexamethasone PO4 0.1%, the moxifloxacin HCl 0.5%, ketorolac tromethamine 0.5% may comprise steps of: (step 101) prepping clean work area (e.g., cleaning and/or disinfecting); (step 102) using only sterilized and/or depyrogenated equipment; (step 103) weighing applicable APIs (e.g., moxifloxacin HCl, the dexamethasone NaPO4 and the ketorolac tromethamine) in a powder hood (with the 0.5%, 0.1% and the 0.5% targets in mind, respectively); (step 104) dissolving the weighed out API powders in sterile water (or WFI) (with the 0.5%, 0.1% and the 0.5% targets in mind, respectively); (step 105) testing and adjusting the pH to a final target of 7.0 to 7.2 via use of HCl, sodium hydroxide, sodium chloride, and a pH meter (calibrated); (step 106) qs ("quantity sufficient") with the sterile water (or WFI) with the 0.5%, 0.1% and the 0.5% targets in mind, respectively; (step 107) transferring resulting solution to a CAI; (step 108) sterile filtering (e.g., using a 0.22 micron filter) the resulting solution to yield the pharmaceutical composition comprising the dexamethasone PO4 0.1%, moxifloxacin HCl 0.5%, ketorolac tromethamine 0.5%; (step 109) QA/QC tests, such as bubble point testing, sterility testing, and/or endotoxin testing; (step 110) filling final container, e.g., a sterile vial; and (step 111) labeling and storage. See e.g., FIG. 1. In some embodiments, step 104 of dissolving weighed out API powders in sterile water (or WFI), i.e., of dissolving the moxifloxacin HCl powder into the water, may be facilitated by adding some HCl (e.g., adding 5 mL of HCl 0.1 N per a 100 mL batch) and stirring for about 20 minutes, at room temperature. Which in some embodiments, may then be followed by adjusting the pH to 6.9 using about 20 mL of sodium hydroxide 1%; and then adding in the sodium chloride, the dexamethasone sodium phosphate, and the ketorolac tromethamine; and then proceeding with step 105 of adjusting the final pH to 7.0 to 7.2. In some embodiments, a 2 mL sterile vial may be used as the final container. In some embodiments, a 2 mL sterile vial may be filled to 1 mL with the pharmaceutical composition.

For example, and without limiting the scope of the present invention, a 100 mL batch of the pharmaceutical composition comprising the dexamethasone PO4 0.1%, moxifloxacin HCl 0.5%, ketorolac tromethamine 0.5% may comprise: 0.523 grams of moxifloxacin HCl; 0.104 grams of dexamethasone sodium PO4; 0.5 grams of ketorolac tromethamine; 0.812 grams of sodium chloride; 1 gram of sodium hydroxide pellets; 1 mL of HCl (1% or 0.1N); and the balance of sterile water (or WFI).

In some embodiments, the pharmaceutical composition may comprise dexamethasone PO4 0.1%, moxifloxacin HCl 0.5%, ketorolac tromethamine 0.5%, sodium chloride, hydrochloric acid, sodium hydroxide, and water; wherein that pharmaceutical composition may have a pH of 7 to 7.2. In some embodiments, this pharmaceutical composition may be preservative free; which may result in increased efficacy as compared to pharmaceutical compositions with preservatives.

In some embodiments, this pharmaceutical composition with the at least three active ingredients (APIs), may have increased efficacy, improved drug delivery, better patient compliance, and have cost savings for patients, as compared against pharmaceutical compositions with only one or two active ingredients (APIs).

In some embodiments, this pharmaceutical composition with dexamethasone PO4 0.1%, moxifloxacin HCl 0.5% and ketorolac tromethamine 0.5% may improve patient compliance by reducing a number treatments.

Discussion of Dexamethasone PO4 0.1%, Moxifloxacin HCL 0.5%, Bromfenac 0.07%

In some embodiments, a pharmaceutical composition may comprise at least three active ingredients (APIs), dexamethasone PO4, moxifloxacin HCl, and bromfenac.

In some embodiments, the dexamethasone may be as discussed above.

In some embodiments, the moxifloxacin HCl may be as discussed above.

In some embodiments, the bromfenac may be known as bromfenac, bromfenac sodium, and bromfenac ophthalmic solution. In some embodiments, the bromfenac may be known as bromfenac sodium sesquihydrate. In some embodiments, the bromfenac may be a nonsteroidal anti-inflammatory drug (NSAID). In some embodiments, bromfenac may block prostaglandin synthesis through cyclooxygenase inhibition, demonstrating COX-2 preference with a lesser affinity for COX-1. In some embodiments, the bromfenac may be used as an analgesic. In some embodiments, bromfenac may be used to treat ocular pain. In some embodiments, bromfenac may be used to treat ocular inflammation. In some embodiments, bromfenac may be used to treat promote and/or facilitate post eye surgery healing and/or health.

In some embodiments, the bromfenac may be present in the pharmaceutical composition at 0.07%; that is, each mL of the pharmaceutical composition may contain 0.07 mg of the bromfenac.

In some embodiments, this pharmaceutical composition may also comprise sodium chloride for purposes of yielding an isotonic, buffered, aqueous solution.

In some embodiments, this pharmaceutical composition may also comprise sodium chloride, sodium hydroxide, and/or hydrochloric acid (HCl) for purposes of adjusting pH of the resulting pharmaceutical composition to a final target pH of 7.0 to 7.2.

In some embodiments, a carrier and/or a solvent of the dexamethasone PO4 0.1%, moxifloxacin HCl 0.5%, bromfenac 0.07% pharmaceutical composition may be water. In some embodiments, this water may be sterile water, water for injection (WFI), or the like.

In some embodiments, the dexamethasone PO4 0.1%, moxifloxacin HCl 0.5%, bromfenac 0.07% pharmaceutical composition may be delivered to the eyes of a patient via use of an injection, as in an intra-cameral injection.

In some embodiments, the dexamethasone PO4 0.1%, moxifloxacin HCl 0.5%, bromfenac 0.07% pharmaceutical composition may be used for post-op care of an eye after cataract surgery of that eye. Such use of the dexamethasone PO4 0.1%, moxifloxacin HCl 0.5%, bromfenac 0.07%, post-op, may minimize post-op infections; and/or may improve recovery from the cataract surgery, both in terms of speed of recovery quality of vision improvement.

In some embodiments, compounding the pharmaceutical composition comprising the dexamethasone PO4 0.1%, the moxifloxacin HCl 0.5%, bromfenac 0.07% may comprise steps of: (step 101) prepping clean work area (e.g., cleaning and/or disinfecting); (step 102) using only sterilized and/or depyrogenated equipment; (step 103) weighing applicable APIs (e.g., moxifloxacin HCl, the dexamethasone NaPO4 and the bromfenac) in a powder hood (with the 0.5%, 0.1% and the 0.07% targets in mind, respectively); (step 104) dissolving the weighed out API powders in sterile water (or WFI) (with the 0.5%, 0.1% and the 0.07% targets in mind, respectively); (step 105) testing and adjusting the pH to a final target of 7.0 to 7.2 via use of HCl, sodium hydroxide, sodium chloride, and a pH meter (calibrated); (step 106) qs ("quantity sufficient") with the sterile water (or WFI) with the 0.5%, 0.1% and the 0.07% targets in mind, respectively; (step 107) transferring resulting solution to a CAI; (step 108) sterile filtering (e.g., using a 0.22 micron filter) the resulting solution to yield the pharmaceutical composition comprising the dexamethasone PO4 0.1%, moxifloxacin HCl 0.5%, bromfenac 0.07%; (step 109) QA/QC tests, such as bubble point testing, sterility testing, and/or endotoxin testing; (step 110) filling final container, e.g., a sterile vial; and (step 111) labeling and storage. In some embodiments, step 104 of dissolving weighed out API powders in sterile water (or WFI), i.e., of dissolving the moxifloxacin HCl powder into the water, may be facilitated by adding some HCl (e.g., adding 5 mL of HCl 0.1 N per a 100 mL batch) and stirring for about 20 minutes, at room temperature. Which in some embodiments, may then be followed by adjusting the pH to 6.9 using about 20 mL of sodium hydroxide 1%; and then adding in the sodium chloride, the dexamethasone sodium phosphate, and the bromfenac; and then proceeding with step 105 of adjusting the final pH to 7.0 to 7.2. In some embodiments, a 2 mL sterile vial may be used as the final container. In some embodiments, a 2 mL sterile vial may be filled to 1 mL with the pharmaceutical composition.

For example, and without limiting the scope of the present invention, a 100 mL batch of the pharmaceutical composition comprising the dexamethasone PO4 0.1%, moxifloxacin HCl 0.5%, bromfenac 0.07% may comprise: 0.523 grams of moxifloxacin HCl; 0.104 grams of dexamethasone sodium PO4; 0.07 grams of bromfenac; 0.812 grams of sodium chloride; 1 gram of sodium hydroxide pellets; 1 mL of HCl (1% or 0.1N); and the balance of sterile water (or WFI).

In some embodiments, the pharmaceutical composition may comprise dexamethasone PO4 0.1%, moxifloxacin HCl 0.5%, bromfenac 0.07%, sodium chloride, hydrochloric acid, sodium hydroxide, and water; wherein that pharmaceutical composition may have a pH of 6.9. In some embodiments, this pharmaceutical composition may be preservative free; which may result in increased efficacy as compared to pharmaceutical compositions with preservatives.

In some embodiments, this pharmaceutical composition with the at least three active ingredients (APIs), may have increased efficacy, improved drug delivery, better patient compliance, and have cost savings for patients, as compared against pharmaceutical compositions with only one or two active ingredients (APIs).

In some embodiments, this pharmaceutical composition with dexamethasone PO4 0.1%, moxifloxacin HCl 0.5% and bromfenac 0.07% may improve patient compliance by reducing a number treatments.

Discussion of Prednisolone PO4 1%, Gatifloxacin 0.5%

In some embodiments, a pharmaceutical composition may comprise at least two active ingredients (APIs), prednisolone PO4 and gatifloxacin.

In some embodiments, prednisolone PO4 may be known as prednisolone, prednisolone phosphate, prednisolone NaPO4, or prednisolone sodium phosphate. In some embodiments, prednisolone PO4 may be prepared to meet USP monograph for prednisolone sodium phosphate ophthalmic solution. In some embodiments, prednisolone PO4 may be an antiinflammatory steroid. A mechanism for action of prednisolone PO4 may be inhibition of migration of polymorphonuclear leukocytes and capilla increase reversal. In some embodiments, prednisolone PO4 may be used for treating inflammation in the eye, at the eye, and/or around the eye via use of eye drops. In some embodiments, prednisolone PO4 may be used post eye surgery. In some embodiments, the pharmaceutical composition containing prednisolone PO4 may have a pH from 6.2 to 8.2. In some embodiments, the prednisolone PO4 may be present in the pharmaceutical composition at 1%; that is each mL (milliliter) of the pharmaceutical composition may contain 11 mg (milligram) of prednisolone PO4.

In some embodiments, gatifloxacin may also be known as gatifloxacin sesquihydrate and gatifloxacin ophthalmic solution. In some embodiments, gatifloxacin may be an antibiotic of the fourth-generation fluoroquinolone family of antibiotics. Mechanism of action of gatifloxacin may be through inhibition of DNA gyrase and topoisomerase IV which may be needed for some bacterial DNA replication, transcription, repair, and recombination. In some embodiments, the gatifloxacin may work by inhibiting bacterial enzymes, specifically, DNA gyrase and topoisomerase IV. In some embodiments, gatifloxacin may be indicated for treatment of bacterial conjunctivitis. In some embodiments, the gatifloxacin may be used for treating bacterial conjunctivitis in eyes. In some embodiments, the gatifloxacin may be used for treating bacterial infections in eyes, at the eyes, and/or around the eyes. In some embodiments, the gatifloxacin may be used to prevent or minimize bacterial growth in the eyes, at the eyes, and/or around the eyes. In some embodiments, gatifloxacin may be used post eye surgery (e.g., Lasik) to prevent or minimize bacterial growth in the eyes, at the eyes, and/or around the eyes. In some embodiments, the gatifloxacin may be present in the pharmaceutical composition at 0.5%; that is each mL of pharmaceutical composition may contain 5.4 mg of gatifloxacin.

In some embodiments, this pharmaceutical composition may also comprise one or more of boric acid (for tonicity adjustment and/or as a preservative of the final preparation), sodium hydroxide (for pH adjustments, e.g., added as 1% NaOH), and/or hydrochloric acid (HCl) (for pH adjustments, e.g., added as 1% or 0.1 N HCl). In some embodiments, the final target pH of this pharmaceutical composition comprising the prednisolone PO4 1% and the gatifloxacin 0.5% may be a pH of 6.5 or 6.8 to 7. In some embodiments, the boric acid may be a weak acid. In some embodiments, the boric acid may have mild antibiotic properties and/or antifungal properties; and thus, act as a preservative. Boric acid solutions may be used to cleanse and/or irrigate eyes (e.g., helping to remove irritants and/or pollutants from the eyes). Boric acid solutions may provide soothing relief to eye irritation. In some embodiments, aqueous solutions of boric acid may help facilitate dissolving of prednisolone sodium PO4.

In some embodiments, a carrier and/or a solvent of the prednisolone PO4 1% and the gatifloxacin 0.5% pharmaceutical composition may be water. In some embodiments, this water may be sterile water, water for irrigation, water for injection (WFI), or the like.

In some embodiments, the prednisolone PO4 1% and the gatifloxacin 0.5% pharmaceutical composition may be delivered to the eyes of a patient via use eye drops from an eye dropper. In some embodiments, a 10 mL ophthalmic drop (e.g., droptainer) may receive a fill volume of this pharmaceutical composition of 3.5 mL.

In some embodiments, the prednisolone PO4 1% and the gatifloxacin 0.5% pharmaceutical composition may be used for post-op eye care after Lasik and the like eye surgeries that may use lasers to mitigate vision problems.

In some embodiments, compounding the pharmaceutical composition comprising the prednisolone PO4 1% and the gatifloxacin 0.5% may comprise steps of: (step 101) prepping clean work area (e.g., cleaning and/or disinfecting); (step 102) using only sterilized and/or depyrogenated equipment; (step 103) weighing applicable APIs (e.g., prednisolone sodium PO4 and gatifloxacin) in a powder hood (with the 1% and the 0.5% targets in mind, respectively); (step 104) dissolving weighed out API powders in sterile water (or WFI) (with the 1% and the 0.5% targets in mind, respectively); (step 105) testing and adjusting the pH to a final target value of 7 via use of sodium hydroxide, and hydrochloric acid, and pH meter (calibrated); (step 106) qs ("quantity sufficient") with the sterile water (or WFI) with the 1% and the 0.5% targets in mind, respectively; (step 107) transferring resulting solution to a CAI; (step 108) sterile filtering (e.g., a 0.22 micron filter) the resulting solution to yield the pharmaceutical composition comprising the prednisolone PO4 1% and the gatifloxacin 0.5%; (step 109) QA/QC tests, such as bubble point testing, sterility testing, and/or endotoxin testing; (step 110) filling final delivery device, e.g., a sterile ophthalmic dropper bottle (e.g., a "drop-tainer," "steri-dropper," or the like); and (step 111) labeling and storage. See e.g., FIG. 1. In some embodiments, the final delivery device, e.g., the sterile ophthalmic dropper bottle, may be light resistant.

In some embodiments, step 104 of dissolving the APIs in the water, the gatifloxacin may be added to acidified water and dissolved prior to adding the prednisolone sodium PO4 to that solution. In some embodiments, step 104 may entail adding 0.1 N HCl to acidify water, then adding and dissolving the gatifloxacin (e.g., via stirring); then adding in the boric acid, NaOH and the prednisolone; wherein the NaOH are added to adjust the final pH to a target of 7. In some embodiments, gatifloxacin powder (solids) may dissolve in water at a pH of 5 or less; however, once dissolved, gatifloxacin may remain in aqueous solution at pH's above 8.5. In some embodiments, the final target pH of this pharmaceutical composition may be from 6.5 to 7.

For example, and without limiting the scope of the present invention, a 100 mL batch of the pharmaceutical composition comprising the prednisolone PO4 1% and the gatifloxacin 0.5% may comprise: 1.186 grams of prednisolone sodium PO4; 0.54 grams of gatifloxacin; 1.25 grams of boric acid; amounts of sodium hydroxide 1% and/or hydrochloric acid 1% or 0.1 N for pH adjustments; and the balance of sterile water (or WFI).

In some embodiments, the pharmaceutical composition may comprise prednisolone PO4 1%, gatifloxacin 0.5%, boric acid, hydrochloric acid, sodium hydroxide, and water; wherein that pharmaceutical composition may have a pH of 6.8 to 7. In some embodiments, a beyond-use date for this pharmaceutical composition may be at least 180 days. And storage may be room temperature. In some embodiments, this pharmaceutical composition may be clear, colorless, and free of visible (with naked eye) particulate matter. In some embodiments, this pharmaceutical composition may be preservative free (aside from the boric acid); which may result in increased efficacy as compared to pharmaceutical compositions with preservatives.

Discussion of Prednisolone PO4 1%, Ketorolac Tromethamine 0.5%

In some embodiments, a pharmaceutical composition may comprise at least two active ingredients (APIs), prednisolone PO4 and ketorolac tromethamine.

In some embodiments, the prednisolone PO4 may be as discussed above.

In some embodiments, the ketorolac tromethamine may be as discussed above, except in this embodiment, the ketorolac tromethamine may be mixed (compounded) with the prednisolone PO4.

In some embodiments, this pharmaceutical composition may also comprise one or more of boric acid (e.g., for tonicity adjustment and/or as a preservative of the final preparation), sodium hydroxide (for pH adjustments, e.g., added as 1% NaOH), and/or hydrochloric acid (HCl) (for pH adjustments, e.g., added as 1% or 0.1 N HCl). In some embodiments, the final target pH of this pharmaceutical composition comprising the prednisolone PO4 1% and the ketorolac tromethamine 0.5% may be a pH of 7.2 to 7.6. In some embodiments, the boric acid may be a weak acid. In some embodiments, the boric acid may have mild antibiotic properties and/or antifungal properties, allowing the boric acid to function as a preservative. Boric acid solutions may be used to cleanse and/or irrigate eyes (e.g., helping to remove irritants and/or pollutants from the eyes). Boric acid solutions may provide soothing relief to eye irritation. In some embodiments, aqueous solutions of boric acid may help facilitate dissolving of prednisolone sodium PO4.

In some embodiments, a carrier and/or a solvent of the prednisolone PO4 1% and the ketorolac tromethamine 0.5% pharmaceutical composition may be water. In some embodiments, this water may be sterile water, water for irrigation, water for injection (WFI), or the like.

In some embodiments, the prednisolone PO4 1% and the ketorolac tromethamine 0.5% pharmaceutical composition may be delivered to the eyes of a patient via use eye drops from an eye dropper. In some embodiments, a 10 mL ophthalmic dropper bottle may receive a fill volume of 4 mL of this prepared pharmaceutical composition.

In some embodiments, the prednisolone PO4 1% and the ketorolac tromethamine 0.5% pharmaceutical composition may be used for post-op eye care for the retina after eye surgery.

In some embodiments, compounding the pharmaceutical composition comprising the prednisolone PO4 1% and the ketorolac tromethamine 0.5% may comprise steps of: (step 101) prepping clean work area (e.g., cleaning and/or disinfecting); (step 102) using only sterilized and/or depyrogenated equipment; (step 103) weighing applicable APIs (e.g., prednisolone sodium PO4 and ketorolac tromethamine) in a powder hood or the like (with the 1% and the 0.5% targets in mind, respectively); (step 104) dissolving weighed out API powders in sterile water (or WFI) (with the 1% and the 0.5% targets in mind, respectively); (step 105) testing and adjusting the pH to a final target value of 7.2 to 7.6 via use of sodium hydroxide, and hydrochloric acid, and pH meter (calibrated); (step 106) qs ("quantity sufficient") with the sterile water (or WFI) with the 1% and the 0.5% targets in mind, respectively; (step 107) transferring resulting solution to a CAI; (step 108) sterile filtering (e.g., a 0.22 micron filter) the resulting solution to yield the pharmaceutical composition comprising the prednisolone PO4 1% and the ketorolac tromethamine 0.5%; (step 109) QA/QC tests, such as clarity, appearance, bubble point testing, sterility testing, and/or endotoxin testing; (step 110) filling final delivery device, e.g., a sterile ophthalmic dropper bottle (e.g., a "drop-tainer," "steri-dropper," or the like); and (step 111) labeling and storage. See e.g., FIG. 1. In some embodiments, the final delivery device, e.g., the sterile ophthalmic dropper bottle, may be light resistant.

For example, and without limiting the scope of the present invention, a 100 mL batch of the pharmaceutical composition comprising the prednisolone PO4 1% and the ketorolac tromethamine 0.5% may comprise: 1.186 grams of prednisolone sodium PO4; 0.50 grams of the ketorolac tromethamine; 1.27 grams of boric acid; amounts of sodium hydroxide 1% and/or hydrochloric acid 1% or 0.1 N for pH adjustments; and the balance of sterile water (or WFI).

In some embodiments, the pharmaceutical composition may comprise prednisolone PO4 1%, ketorolac tromethamine 0.5%, boric acid, hydrochloric acid, sodium hydroxide, and water; wherein that pharmaceutical composition may have a pH of 7.2 to 7.6 (or pH 7.2 to 7.4). In some embodiments, this pharmaceutical composition may have a beyond-use date of at least 180 days. Storage may be room temperature. In some embodiments, this pharmaceutical composition may be clear, colorless, and free of visible (with naked eye) particulate matter. In some embodiments, this pharmaceutical composition may be preservative free (aside from the boric acid); which may result in increased efficacy as compared to pharmaceutical compositions with preservatives.

Discussion of Prednisolone PO4 1%, Ketorolac Tromethamine 0.5%, Gatifloxacin 0.5%

In some embodiments, a pharmaceutical composition may comprise at least three active ingredients (APIs), prednisolone PO4, ketorolac tromethamine, and gatifloxacin.

In some embodiments, the prednisolone PO4 may be as discussed above.

In some embodiments, the ketorolac tromethamine may be as discussed above, except in this embodiment, the ketorolac tromethamine may be mixed (compounded) with the prednisolone PO4 and with gatifloxacin.

In some embodiments, the gatifloxacin may be as discussed above.

In some embodiments, this pharmaceutical composition may also comprise one or more of boric acid (for tonicity adjustment), sodium hydroxide (for pH adjustment, e.g., added as 5% NaOH), and/or hydrochloric acid (HCl) (for pH adjustment, e.g., added as 1% or 0.1 N HCl). In some embodiments, the final target pH of this pharmaceutical composition comprising the prednisolone PO4 1%, the ketorolac tromethamine 0.5%, and the gatifloxacin 0.5% may be a pH of 8.5 or greater. In some embodiments, the boric acid may be a weak acid. In some embodiments, the boric acid may have mild antibiotic properties and/or antifungal properties, such that this boric acid may function as a preservative. Boric acid solutions may be used to cleanse and/or irrigate eyes (e.g., helping to remove irritants and/or pollutants from the eyes). Boric acid solutions may provide soothing relief to eye irritation. In some embodiments, aqueous solutions of boric acid may help facilitate dissolving of prednisolone sodium PO4.

In some embodiments, a carrier and/or a solvent of the prednisolone PO4 1%, the ketorolac tromethamine 0.5%, and the gatifloxacin 0.5% pharmaceutical composition may be water. In some embodiments, this water may be sterile water, water for irrigation, water for injection (WFI), or the like.

In some embodiments, the prednisolone PO4 1%, the ketorolac tromethamine 0.5%, and the gatifloxacin 0.5% pharmaceutical composition may be delivered to the eyes of a patient via use eye drops from an eye dropper. In some embodiments, a fill volume of 3.5 mL or 6.5 mL of this pharmaceutical composition may be contained in a 10 mL ophthalmic dropper (e.g., droptainer or the like).

In some embodiments, the prednisolone PO4 1%, the ketorolac tromethamine 0.5%, and the gatifloxacin 0.5% pharmaceutical composition may be used for post-op eye care after cataract surgery.

In some embodiments, compounding the pharmaceutical composition comprising the prednisolone PO4 1%, the ketorolac tromethamine 0.5%, and the gatifloxacin 0.5% may comprise steps of: (step 101) prepping clean work area (e.g., cleaning and/or disinfecting); (step 102) using only sterilized and/or depyrogenated equipment; (step 103) weighing applicable APIs (e.g., prednisolone sodium PO4, ketorolac tromethamine, and gatifloxacin) in a powder hood (with the 1%, the 0.5%, and the 0.5% targets in mind, respectively); (step 104) dissolving weighed out API powders in sterile water (or WFI) (with the 1%, the 0.5%, and the 0.5% targets in mind, respectively); (step 105) testing and adjusting the pH to a final target value of 8.5 or greater via use of sodium hydroxide, and hydrochloric acid, and pH meter (calibrated); (step 106) qs ("quantity sufficient") with the sterile water (or WFI) with the 1%, the 0.5%, and the 0.5% targets in mind, respectively; (step 107) transferring resulting solution to a CAI; (step 108) sterile filtering (e.g., a 0.22 micron filter) the resulting solution to yield the pharmaceutical composition comprising the prednisolone PO4 1%, the ketorolac tromethamine 0.5%, and the gatifloxacin 0.5%; (step 109) QA/QC tests, such as bubble point testing, sterility testing, and/or endotoxin testing; (step 110) filling final delivery device, e.g., a sterile ophthalmic dropper bottle (e.g., a "drop-tainer," "steri-dropper," or the like); and (step 111) labeling and storage. See e.g., FIG. 1. In some embodiments, the final delivery device, e.g., the sterile ophthalmic dropper bottle, may be light resistant. In some embodiments, the final delivery device may have a total volume of 15 mL with a fill volume of 6.5 mL. In some embodiments, the final delivery device may be stored at room temperature.

In some embodiments, step 104 of dissolving the APIs in the water, the gatifloxacin may be added to acidified water and dissolved prior to adding of the dissolved ketorolac tromethamine and the dissolved prednisolone sodium PO4. In some embodiments, step 104 may entail adding 0.1 N HCl to acidify water, then adding and dissolving the gatifloxacin (e.g., via stirring); and then adding NaOH to bring the pH up to 8.5. In some embodiments, gatifloxacin powder (solids) may dissolve in water at a pH of 5 or less; however, once dissolved, gatifloxacin may remain in aqueous solution at pH's above 8.5. In some embodiments, the ketorolac tromethamine may be dissolved separately (separately from dissolving the other APIs) in a volume of water (no need to acidify). In some embodiments, the prednisolone PO4 may be dissolved separately (separately from dissolving the other APIs) in a volume of water with the boric acid. In some embodiments, once the gatifloxacin has been dissolved and its pH brought up to 8.5; then the dissolved ketorolac tromethamine may be slowly added to the solution; then the pH may be tested to check if the pH is at or above 8.5; and if the pH is too low it may be adjusted with NaOH (e.g., NaOH 5%) to the 8.5 or above level; and then the dissolved prednisolone PO4 with boric acid may be added to the dissolved gatifloxacin with the dissolved ketorolac tromethamine solution, again testing and making sure the pH remains at or above 8.5. A pH below 8.2 or below 8.3 may result in irreversible and undesirable precipitate.

For example, and without limiting the scope of the present invention, a 100 mL batch of the pharmaceutical composition comprising the prednisolone PO4 1%, the ketorolac tromethamine 0.5%, and the gatifloxacin 0.5% may comprise: 1.186 grams of prednisolone sodium PO4; 0.50 grams of the ketorolac tromethamine; 0.54 grams of gatifloxacin; 0.95 grams of boric acid; amounts of sodium hydroxide 5% and/or hydrochloric acid 1% or 0.1 N for pH adjustments; and the balance of sterile water (or WFI).

In some embodiments, the pharmaceutical composition may comprise prednisolone PO4 1%, gatifloxacin 0.5%, ketorolac tromethamine 0.5%, boric acid, hydrochloric acid, sodium hydroxide, and water; wherein that pharmaceutical composition may have a pH of 8.5 or above. In some embodiments, a beyond-use date of at least 180 days may be applicable for this pharmaceutical composition. And this pharmaceutical composition may be stored at room temperature. In some embodiments, this pharmaceutical composition may be clear and yellowish in appearance. In some embodiments, this pharmaceutical composition may be preservative free (aside from the boric acid); which may result in increased efficacy as compared to pharmaceutical compositions with preservatives.

In some embodiments, this pharmaceutical composition with the at least three active ingredients (APIs), may have increased efficacy, improved drug delivery, better patient compliance, and have cost savings for patients, as compared against pharmaceutical compositions with only one or two active ingredients (APIs).

Discussion of Prednisolone PO4 1%, Bromfenac 0.07%

In some embodiments, a pharmaceutical composition may comprise at least two active ingredients (APIs), prednisolone PO4 and bromfenac.

In some embodiments, the prednisolone PO4 may be as discussed above.

In some embodiments, the bromfenac may be as discussed above, except in this embodiment, the bromfenac may be mixed (compounded) with the prednisolone PO4.

In some embodiments, this pharmaceutical composition may also comprise one or more of boric acid (for tonicity adjustment), sodium hydroxide (for pH adjustment, e.g., added as 1% NaOH), and/or hydrochloric acid (HCl) (for pH adjustment, e.g., added as 1% or 0.1 N HCl). In some embodiments, the final target pH of this pharmaceutical composition comprising the prednisolone PO4 1% and the bromfenac 0.07% may be a pH of 6.8 to 7. In some embodiments, the final target pH of this pharmaceutical composition comprising the prednisolone PO4 1% and the bromfenac 0.07% may be a pH of 8.3 to 8.5. In some embodiments, the boric acid may be a weak acid. In some embodiments, the boric acid may have mild antibiotic properties and/or antifungal properties, such that the boric acid functions as a preservative. Boric acid solutions may be used to cleanse and/or irrigate eyes (e.g., helping to remove irritants and/or pollutants from the eyes). Boric acid solutions may provide soothing relief to eye irritation. In some embodiments, aqueous solutions of boric acid may help facilitate dissolving of prednisolone sodium PO4.

In some embodiments, a carrier and/or a solvent of the prednisolone PO4 1% and the bromfenac 0.07% pharmaceutical composition may be water. In some embodiments, this water may be sterile water, water for irrigation, water for injection (WFI), or the like.

In some embodiments, the prednisolone PO4 1% and the bromfenac 0.07% pharmaceutical composition may be delivered to the eyes of a patient via use eye drops from an eye dropper. In some embodiments, a fill volume of 4 mL of this pharmaceutical composition may be contained within a 10 mL ophthalmic dropper (e.g., droptainer or the like).

In some embodiments, the prednisolone PO4 1% and the bromfenac 0.07% pharmaceutical composition may be used for post-op eye care for the retina after eye surgery.

In some embodiments, compounding the pharmaceutical composition comprising the prednisolone PO4 1% and the bromfenac 0.07% may comprise steps of: (step 101) prepping clean work area (e.g., cleaning and/or disinfecting); (step 102) using only sterilized and/or depyrogenated equipment; (step 103) weighing applicable APIs (e.g., prednisolone sodium PO4 and bromfenac) in a powder hood (with the 1% and the 0.07% targets in mind, respectively); (step 104) dissolving weighed out API powders in sterile water (or WFI) (with the 1% and the 0.07% targets in mind, respectively); (step 105) testing and adjusting the pH to a final target value of 6.8 to 7 via use of sodium hydroxide, and hydrochloric acid, and pH meter (calibrated); (step 106) qs ("quantity sufficient") with the sterile water (or WFI) with the 1% and the 0.07% targets in mind, respectively; (step 107) transferring resulting solution to a CAI; (step 108) sterile filtering (e.g., a 0.22 micron filter) the resulting solution to yield the pharmaceutical composition comprising the prednisolone PO4 1% and the bromfenac 0.07%; (step 109) QA/QC tests, such as bubble point testing, sterility testing, and/or endotoxin testing; (step 110) filling final delivery device, e.g., a sterile ophthalmic dropper bottle (e.g., a "drop-tainer," "steri-dropper," or the like); and (step 111) labeling and storage. See e.g., FIG. 1. In some embodiments, the final delivery device, e.g., the sterile ophthalmic dropper bottle, may be light resistant. In some embodiments, the final delivery device may be stored at room temperature.

In some embodiments, step 104 of dissolving the APIs, particularly dissolving the prednisolone PO4, may be facilitated by use of an aqueous solution of boric acid.

For example, and without limiting the scope of the present invention, a 100 mL batch of the pharmaceutical composition comprising the prednisolone PO4 1% and the bromfenac 0.07% may comprise: 1.125 grams of prednisolone sodium PO4; 0.07 grams of the bromfenac; 1.25 grams of boric acid; amounts of sodium hydroxide 1% and/or hydrochloric acid 1% or 0.1 N for pH adjustments; and the balance of sterile water (or WFI).

In some embodiments, the pharmaceutical composition may comprise prednisolone PO4 1%, bromfenac 0.07%, boric acid, hydrochloric acid (optionally if needed for pH adjustment), sodium hydroxide, and water; wherein that pharmaceutical composition may have a pH of 6.8 to 7.

In some embodiments, the pharmaceutical composition may comprise prednisolone PO4 1%, bromfenac 0.07%, boric acid, hydrochloric acid (optionally if needed for pH adjustment), sodium hydroxide, and water; wherein that pharmaceutical composition may have a pH of 8.3 to 8.5.

In some embodiments, the pharmaceutical composition may comprise prednisolone PO4 1%, bromfenac 0.07%, boric acid, hydrochloric acid (optionally if needed for pH adjustment), sodium hydroxide, and water; wherein this pharmaceutical composition may have a beyond-use date of at least 180 days. And this pharmaceutical composition may be stored at room temperature.

In some embodiments, the pharmaceutical composition may comprise prednisolone PO4 1%, bromfenac 0.07%, boric acid, hydrochloric acid (optionally if needed for pH adjustment), sodium hydroxide, and water; wherein this pharmaceutical composition may have a beyond-use date of at least 180 days. And this pharmaceutical composition may be stored at room temperature. In some embodiments, this pharmaceutical composition may be clear and yellowish in appearance.

In some embodiments, this pharmaceutical composition comprising the prednisolone PO4 1% and the bromfenac 0.07% may be preservative free (aside from the boric acid); which may result in increased efficacy as compared to pharmaceutical compositions with preservatives.

Discussion of Prednisolone PO4 1%, Gatifloxacin 0.5%, Bromfenac 0.07%

In some embodiments, a pharmaceutical composition may comprise at least three active ingredients (APIs), prednisolone PO4, gatifloxacin, and bromfenac.

In some embodiments, the prednisolone PO4 may be as discussed above.

In some embodiments, the gatifloxacin may be as discussed above, except in this embodiment, the gatifloxacin may be mixed (compounded) with the prednisolone PO4 and with the bromfenac.

In some embodiments, the bromfenac may be as discussed above, except in this embodiment, the bromfenac may be mixed (compounded) with the prednisolone PO4 and with the gatifloxacin.

In some embodiments, this pharmaceutical composition may also comprise one or more of boric acid (for osmotic adjustment and/or as a preservative), sodium hydroxide (for pH adjustment, e.g., added as 1% NaOH), and/or hydrochloric acid (HCl) (for pH adjustment, e.g., added as 1% or 0.1 N HCl). In some embodiments, the final target pH of this pharmaceutical composition comprising the prednisolone PO4 1%, gatifloxacin 0.5%, and the bromfenac 0.07% may be a pH of 6.8 to 7. In some embodiments, the final target pH of this pharmaceutical composition comprising the prednisolone PO4 1%, gatifloxacin 0.5%, and the bromfenac 0.07% may be a pH of 8.3. In some embodiments, the boric acid may be a weak acid. In some embodiments, the boric acid may have mild antibiotic properties and/or antifungal properties, such that this boric acid functions as a preservative. Boric acid solutions may be used to cleanse and/or irrigate eyes (e.g., helping to remove irritants and/or pollutants from the eyes). Boric acid solutions may provide soothing relief to eye irritation. In some embodiments, aqueous solutions of boric acid may help facilitate dissolving of prednisolone sodium PO4.

In some embodiments, a carrier and/or a solvent of the prednisolone PO4 1%, gatifloxacin 0.5%, and the bromfenac 0.07% pharmaceutical composition may be water. In some embodiments, this water may be sterile water, water for irrigation, water for injection (WFI), or the like.

In some embodiments, the prednisolone PO4 1%, gatifloxacin 0.5%, and the bromfenac 0.07% pharmaceutical composition may be delivered to the eyes of a patient via use eye drops from an eye dropper. In some embodiments, a fill volume of 3.5 mL or 6.5 mL of this pharmaceutical composition may be contained within a 10 mL ophthalmic dropper (e.g., a droptainer or the like).

In some embodiments, the prednisolone PO4 1%, gatifloxacin 0.5%, and the bromfenac 0.07% pharmaceutical composition may be used for post-op eye care after cataract surgery.

In some embodiments, compounding the pharmaceutical composition comprising the prednisolone PO4 1%, the gatifloxacin 0.5%, and the bromfenac 0.07% may comprise steps of: (step 101) prepping clean work area (e.g., cleaning and/or disinfecting); (step 102) using only sterilized and/or depyrogenated equipment; (step 103) weighing applicable APIs (e.g., prednisolone sodium PO4, gatifloxacin, and bromfenac) in a powder hood (with the 1%, 0.5%, and the 0.07% targets in mind, respectively); (step 104) dissolving weighed out API powders in sterile water (or WFI) (with the 1%, 0.5%, and the 0.07% targets in mind, respectively); (step 105) testing and adjusting the pH to a final target value of 6.8 to 7 via use of sodium hydroxide, and hydrochloric acid, and pH meter (calibrated); (step 106) qs ("quantity sufficient") with the sterile water (or WFI) with the 1%, 0.5%, and the 0.07% targets in mind, respectively; (step 107) transferring resulting solution to a CAI; (step 108) sterile filtering (e.g., a 0.22 micron filter) the resulting solution to yield the pharmaceutical composition comprising the prednisolone PO4 1%, the gatifloxacin 0.5%, and the bromfenac 0.07%; (step 109) QA/QC tests, such as bubble point testing, sterility testing, and/or endotoxin testing; (step 110) filling final delivery device, e.g., a sterile ophthalmic dropper bottle (e.g., a "drop-tainer," "steri-dropper," or the like); and (step 111) labeling and storage. See e.g., FIG. 1. In some embodiments, the final delivery device, e.g., the sterile ophthalmic dropper bottle, may be light resistant. In some embodiments, the final delivery device may be stored at room temperature.

In some embodiments, step 104 of dissolving the APIs in the water, the gatifloxacin may be added to acidified water and dissolved prior to adding the prednisolone sodium PO4 to that solution. In some embodiments, step 104 may entail adding 0.1 N HCl to acidify water, then adding and dissolving the gatifloxacin (e.g., via stirring); then adding in the boric acid, NaOH and the prednisolone PO4; and the bromfenac; the NaOH are added to adjust the final pH to a target of 6.8 to 7. In some embodiments, gatifloxacin powder (solids) may dissolve in water at a pH of 5 or less; however, once dissolved, gatifloxacin may remain in aqueous solution at pH's above 8.5.

In some embodiments, step 104 of dissolving the APIs, particularly dissolving the prednisolone PO4, may be facilitated by use of an aqueous solution of boric acid.

For example, and without limiting the scope of the present invention, a 100 mL batch of the pharmaceutical composition comprising the prednisolone PO4 1%, the gatifloxacin 0.5%, and the bromfenac 0.07% may comprise: 1.186 grams of prednisolone sodium PO4; 0.54 grams of gatifloxacin; 0.07 grams of the bromfenac; 0.95 IU of boric acid; amounts of sodium hydroxide 1% (e.g., 1 gram of NaOH pellets) and/or hydrochloric acid 1% or 0.1 N (e.g., 1 mL) for pH adjustments; and the balance of sterile water (or WFI).

In some embodiments, the pharmaceutical composition may comprise prednisolone PO4 1%, gatifloxacin 0.5%, bromfenac 0.07%, boric acid, hydrochloric acid (optionally if needed for pH adjustment), sodium hydroxide, and water; wherein that pharmaceutical composition may have a pH of 6.8 to 7.

In some embodiments, the pharmaceutical composition may comprise prednisolone PO4 1%, gatifloxacin 0.5%, bromfenac 0.07%, boric acid, hydrochloric acid (optionally if needed for pH adjustment), sodium hydroxide, and water; wherein that pharmaceutical composition may have a pH of 8.3. In some embodiments, this pharmaceutical composition may be clear and yellowish in appearance. In some embodiments, this pharmaceutical composition may have a beyond-use date of at least 180 days. And this pharmaceutical composition may be stored at room temperature.

In some embodiments, this pharmaceutical composition may be preservative free (aside from the boric acid); which may result in increased efficacy as compared to pharmaceutical compositions with preservatives.

In some embodiments, this pharmaceutical composition with the at least three active ingredients (APIs), may have increased efficacy, improved drug delivery, better patient compliance, and have cost savings for patients, as compared against pharmaceutical compositions with only one or two active ingredients (APIs).

Discussion of Prostaglandin E2 (PGE2) and ACE

In some embodiments, a pharmaceutical composition may comprise an amniotic cytokine extract (ACE), that may comprise prostaglandin2 (PGE2). In some embodiments, prostaglandin2 may also be known as prostaglandin E2 or as PGE2. In some embodiments, prostaglandin E2 may be a natural prostaglandin source. Prostaglandins may be lipids or lipid like chemicals and may act or function as hormones in vertebrates. In some embodiments, the amniotic cytokine extract (ACE), may comprise natural prostaglandin E2 (PGE2) at 10,000 pg/mL. In some embodiments, the ACE may comprise cytokines, growth factors, and antiinflammatory molecules. In some embodiments, the ACE may comprise thrombosonndin-1 (TSP-1), WNT4, PGE2, and GDF11. Cytokines, growth factors, and anti-inflammatory molecules in ACE may play a natural role in natural wound healing and tissue growth.

In some embodiments, the pharmaceutical composition that may comprise ACE and/or PGE2, may be used for the treatment of dry eyes. In some embodiments, the ACE and/or PGE2 may promote tear film, restore tear film, increase tear production, and/or reduce ocular inflammation. In some embodiments, the ACE and/or PGE2 may promote and/or facilitate eyelash growth and/or development.

In some embodiments, the pharmaceutical composition comprising the ACE and/or the PGE2, may also comprise BSS (balanced salt solution). In some embodiments, the BSS may be balanced for ocular use. In some embodiments, the BSS may be an intraocular solution. In some embodiments, the BSS may comprise sodium chloride, potassium chloride, calcium chloride dehydrate, magnesium chloride hexahydrate, sodium acetate trihydrate, sodium citrate dihydrate, sodium hydroxide and/or hydrochloric acid (to adjust pH), and water for injection (WFI). In some embodiments, the BSS may have a pH of substantially 7 to 7.5. In some embodiments, the BSS may have an osmolality of substantially 300 mOsm/Kg. In some embodiments, the BSS may be sterile and/or aseptically filled. For example, and without limiting the scope of the present invention, in some embodiments, each mL of BSS may comprise: sodium chloride (NaCl) 0.64%, potassium chloride (KCl) 0.075%, calcium chloride dihydrate (CaCl2.2H2O) 0.048%, magnesium chloride hexahydrate (MgCl2.6H2O) 0.03%, sodium acetate trihydrate (C2H3NaO2.3H2O) 0.39%, sodium citrate dihydrate (C6H5Na3O7.2H2O) 0.17%, sodium hydroxide and/or hydrochloric acid (to adjust pH), and WFI. Other similar, but slightly different, formulations of BSS may be used as well.

In some embodiments, the pharmaceutical composition comprising the ACE and/or the PGE2, and the BSS, may comprise the (1) ACE and/or the PGE2 and (2) the BSS in equal volumes of the (1) and the (2). For example, and without limiting the scope of the present invention, a 300 mL batch of this pharmaceutical composition may comprise 150 mL of ACE (or 150 mL of PGE2) and 150 mL of BSS.

In some embodiments, the ACE (and/or PGE2) and the BSS pharmaceutical composition may be delivered to the eyes of a patient via use eye drops from an eye dropper. In some embodiments, the ACE (and/or PGE2) and the BSS pharmaceutical composition may be delivered to the eyes of a patient via an intra-cameral injection to the eye.

In some embodiments, the ACE (and/or PGE2) and the BSS pharmaceutical composition may be used for treating dry eyes.

In some embodiments, compounding the pharmaceutical composition comprising the ACE (and/or PGE2) and the BSS may comprise steps of: (step 201) prepping clean work area (e.g., cleaning and/or disinfecting); (step 202) using only sterilized and/or depyrogenated equipment; (step 203) pre-staging the final delivery devices, e.g., sterile ophthalmic dropper bottles (e.g., "drop-tainers," "steri-droppers," or the like) and including pre-labeling of these final delivery devices; (step 204) thawing out ACE (and/or PGE2) solution using room temperature water bath; (step 205) adding an equal volume of the BSS to the thawed out solution of ACE (and/or PGE2); (step 206) using CAI and aseptic filling techniques, filling the final delivery devices (e.g., which can include use of a repeater pump); (step 207) QA/QC (quality assurance/quality control) tests, such as sterility testing, pyrogen testing, and/or endotoxin testing; and (step 208) freeze and store frozen at −20 Celsius (Centigrade). See e.g., FIG. 2. In some embodiments, the frozen filled final delivery device should be shipped while frozen (e.g., by use of dry ice) and stored while frozen. In some embodiments, fills of the final delivery device may be at 1 mL or 0.5 mL fill into a 3 mL final delivery device.

In some embodiments, this pharmaceutical composition of ACE (and/or of PGE2) and the BSS, may result in minimal burning, stinging, and/or taste.

In some embodiments, each formulation (e.g., each pharmaceutical composition) disclosed herein, may be compounded and/or filled using aseptic compounding and filling techniques.

In some embodiments, a step of transferring a resulting solution to the CAI (e.g., the compounding aseptic isolator) (e.g., step 107) may be replaced by performing all of the compounding and filling steps in a CAI; and/or performing all of the compounding and filling steps in a clean room; and/or performing all of the compounding and filling steps in a laminar flow hood.

In some embodiments, a step of transferring a resulting solution to the CAI (e.g., the compounding aseptic isolator) (e.g., step 107) may be replaced by performing all or a subset of the compounding and filling steps in a CAI; and/or performing all or a subset of the compounding and filling steps in a clean room; and/or performing all or a subset of the compounding and filling steps in a laminar flow hood.

Discussion of Phenylephrine HCl 1.5%, Lidocaine HCl 1%, Ketorolac Tromethamine 0.3%

In some embodiments, a pharmaceutical composition may comprise at least three active ingredients (APIs): phenylephrine HCl, lidocaine HCl, and ketorolac tromethamine.

In some embodiments, the phenylephrine HCl may be a directly acting sympathmimetic agent (e.g., with a-adrenergic effects) used in the eye as a mydriatic agent (e.g., to dilate the eye's pupil). In the eye, phenylephrine HCl may constrict ophthalmic blood vessels and the radial muscle of the iris.

In some embodiments, the phenylephrine HCl may be present in the pharmaceutical composition at 1.5%; that is, each mL of the pharmaceutical composition may contain 15 mg of the phenylephrine HCl.

In some embodiments, the lidocaine HCl may be a local anesthetic that may reduce pain and/or reduce discomfort during a medical procedure, such as eye surgery, while the lidocaine HCl remains active.

In some embodiments, the lidocaine HCl may be present in the pharmaceutical composition at 1%; that is, each mL of the pharmaceutical composition may contain 10 mg of the lidocaine HCl.

In some embodiments, the ketorolac tromethamine may be a non-steroidal antiinflammatory drug (NSAID), in the family of heterocyclic acetic acid derivatives. In some embodiments, the ketorolac tromethamine may be used as an analgesic.

In some embodiments, the ketorolac tromethamine may be present in the pharmaceutical composition at 0.3%; that is, each mL of the pharmaceutical composition may contain 3 mg of the ketorolac tromethamine.

In some embodiments, this pharmaceutical composition may also comprise sodium chloride for purposes of yielding an isotonic, buffered, aqueous solution.

In some embodiments, this pharmaceutical composition may also comprise sodium chloride, sodium hydroxide, and/or hydrochloric acid (HCl) for purposes of adjusting pH of the resulting pharmaceutical composition to a final target pH of 6.5.

In some embodiments, a carrier and/or a solvent of the phenylephrine HCl 1.5%, lidocaine HCl 1%, ketorolac tromethamine 0.3% pharmaceutical composition may be water. In some embodiments, this water may be sterile water, water for injection (WFI), or the like.

In some embodiments, the phenylephrine HCl 1.5%, lidocaine HCl 1%, ketorolac tromethamine 0.3% pharmaceutical composition may be delivered to the eyes of a patient via use of an injection, as in an intra-cameral injection.

In some embodiments, the phenylephrine HCl 1.5%, lidocaine HCl 1%, ketorolac tromethamine 0.3% pharmaceutical composition may be used pre-op in preparation for eye surgery, such as, but not limited to, cataract surgery of an eye. In some embodiments, the phenylephrine HCl 1.5%, lidocaine HCl 1%, ketorolac tromethamine 0.3% pharmaceutical composition may be used during eye surgery, such as, but not limited to, cataract surgery of an eye. Such uses of the phenylephrine HCl 1.5%, lidocaine HCl 1%, ketorolac tromethamine 0.3% pharmaceutical composition, may minimize post-op infections; and/or may improve recovery from the eye surgery, both in terms of speed of recovery and quality of vision improvement.

In some embodiments, compounding the pharmaceutical composition comprising the phenylephrine HCl 1.5%, lidocaine HCl 1%, ketorolac tromethamine 0.3% may comprise steps of: (step 101) prepping clean work area (e.g., cleaning and/or disinfecting); (step 102) using only sterilized and/or depyrogenated equipment; (step 103) weighing applicable APIs (e.g., the phenylephrine HCl, the lidocaine HCl, and the ketorolac tromethamine) in a powder hood (with the 1.5%, 1% and the 0.3% targets in mind, respectively); (step 104) dissolving the weighed out API powders in sterile water (or WFI) (with the 1.5%, 1% and the 0.3% targets in mind, respectively); (step 105) testing and adjusting the pH to a final target of 6.5 via use of HCl, sodium hydroxide, sodium chloride, and a pH meter (calibrated); (step 106) qs ("quantity sufficient") with the sterile water (or WFI) with the 1.5%, 1% and the 0.3% targets in mind, respectively; (step 107) transferring resulting solution to a CAI; (step 108) sterile filtering (e.g., using a 0.22 micron filter) the resulting solution to yield the pharmaceutical composition comprising the phenylephrine HCl 1.5%, the lidocaine HCl 1%, and the ketorolac tromethamine 0.3% as the APIs; (step 109) QA/QC tests, such as bubble point testing, sterility testing, and/or endotoxin testing; (step 110) filling final container, e.g., a sterile vial; and (step 111) labeling and storage. See e.g., FIG. 1. In some embodiments, a 5 mL sterile vial may be used as the final container. In some embodiments, a 5 mL sterile vial may be filled to 4 mL with the pharmaceutical composition of phenylephrine HCl 1.5%, lidocaine HCl 1%, and ketorolac tromethamine 0.3%.

For example, and without limiting the scope of the present invention, a 2050 mL batch of the pharmaceutical composition comprising the phenylephrine HCl 1.5%, lidocaine HCl 1%, and ketorolac tromethamine 0.3% may comprise: 30.75 grams of phenylephrine HCl; 21 grams of lidocaine HCl; 6.15 grams of ketorolac tromethamine; 4.9 grams of sodium chloride; possibly sodium hydroxide pellets and/or HCl (1% or 0.1N) for adjusting final pH to 6.5; and the balance of sterile water (or WFI).

In some embodiments, the pharmaceutical composition may comprise phenylephrine HCl 1.5%, lidocaine HCl 1%, ketorolac tromethamine 0.3%, sodium chloride, water, and/or hydrochloric acid (for pH adjustments), and/or sodium hydroxide (for pH adjustments); wherein that pharmaceutical composition may have a pH of 6.5. In some embodiments, this pharmaceutical composition may be preservative free; which may result in increased efficacy as compared to pharmaceutical compositions with preservatives.

In some embodiments, this pharmaceutical composition with the at least three active ingredients (APIs) (e.g., phenylephrine HCl 1.5%, lidocaine HCl 1%, and ketorolac tromethamine 0.3%), may have increased efficacy, improved drug delivery, better patient compliance, and have cost savings for patients, as compared against pharmaceutical compositions with only one or two active ingredients (APIs).

Discussion of Phenylephrine HCl 1.5%, Lidocaine HCl 1%, Bromfenac 0.01%

In some embodiments, a pharmaceutical composition may comprise at least three active ingredients (APIs): phenylephrine HCl, lidocaine HCl, and bromfenac.

In some embodiments, the phenylephrine HCl may be a directly acting sympathmimetic agent (e.g., with a-adrenergic effects) used in the eye as a mydriatic agent (e.g., to dilate the eye's pupil). In the eye, phenylephrine HCl may constrict ophthalmic blood vessels and the radial muscle of the iris.

In some embodiments, the phenylephrine HCl may be present in the pharmaceutical composition at 1.5%; that is, each mL of the pharmaceutical composition may contain 15 mg of the phenylephrine HCl.

In some embodiments, the lidocaine HCl may be a local anesthetic that may reduce pain and/or reduce discomfort during a medical procedure, such as eye surgery, while the lidocaine HCl remains active.

In some embodiments, the lidocaine HCl may be present in the pharmaceutical composition at 1%; that is, each mL of the pharmaceutical composition may contain 10 mg of the lidocaine HCl.

In some embodiments, the bromfenac may be a nonsteroidal anti-inflammatory drug (NSAID). In some embodiments, the bromfenac may be used as an analgesic.

In some embodiments, the bromfenac may be present in the pharmaceutical composition at 0.07%; that is, each mL of the pharmaceutical composition may contain 0.07 mg of the bromfenac.

In some embodiments, the bromfenac may be present in the pharmaceutical composition at 0.01%.

In some embodiments, this pharmaceutical composition may also comprise sodium chloride for purposes of yielding an isotonic, buffered, aqueous solution.

In some embodiments, this pharmaceutical composition may also comprise sodium chloride, sodium hydroxide, and/or hydrochloric acid (HCl) for purposes of adjusting pH of the resulting pharmaceutical composition. In some embodiments, pH may be adjusted to a final target pH of 7.0 to 7.2.

In some embodiments, a carrier and/or a solvent of the phenylephrine HCl 1.5%, lidocaine HCl 1%, bromfenac 0.01% pharmaceutical composition may be sterile water. In some embodiments, this water may be sterile water, water for injection (WFI), or the like.

In some embodiments, the phenylephrine HCl 1.5%, lidocaine HCl 1%, and bromfenac 0.01% pharmaceutical composition may be indicated for pupil dilation and/or pain relief during and/or after eye surgery, such as, but not limited to cataract surgery.

In some embodiments, the phenylephrine HCl 1.5%, lidocaine HCl 1%, bromfenac 0.01% pharmaceutical composition may be delivered to the eye(s) of a patient via use of an injection, as in an intra-cameral injection.

In some embodiments, the phenylephrine HCl 1.5%, lidocaine HCl 1%, bromfenac 0.01% pharmaceutical composition may be used pre-op in preparation for eye surgery, such as, but not limited to, cataract surgery of an eye. In some embodiments, the phenylephrine HCl 1.5%, lidocaine HCl 1%, bromfenac 0.01% pharmaceutical composition may be used during eye surgery, such as, but not limited to, cataract surgery of an eye. Such uses of the phenylephrine HCl 1.5%, lidocaine HCl 1%, bromfenac 0.01% pharmaceutical composition, may minimize post-op infections; and/or may improve recovery from the eye surgery, both in terms of speed of recovery and quality of vision improvement.

In some embodiments, the pharmaceutical composition may comprise phenylephrine HCl 1.5%, lidocaine HCl 1%, bromfenac 0.01%, sodium chloride, sterile water, and/or hydrochloric acid (for pH adjustments), and/or sodium hydroxide (for pH adjustments); wherein that pharmaceutical composition may have a final target pH of 7.0 to 7.2. In some embodiments, this pharmaceutical composition may be preservative free; which may result in increased efficacy as compared to pharmaceutical compositions with preservatives.

In some embodiments, this pharmaceutical composition with the at least three active ingredients (APIs) (e.g., phenylephrine HCl 1.5%, lidocaine HCl 1%, and bromfenac 0.01%), may have increased efficacy, improved drug delivery, better patient compliance, and have cost savings for patients, as compared against pharmaceutical compositions with only one or two active ingredients (APIs).

In the following discussion that addresses a number of embodiments and applications of the present invention, reference is made to the accompanying drawings that form a part thereof, where depictions are made, by way of illustration, of specific embodiments in which the invention may be practiced. It is to be understood that other embodiments may be utilized and changes may be made without departing from the scope of the invention.

FIG. 1 may depict a flow diagram of a method 100; wherein method 100 may comprise the steps for compounding and/or filling a given pharmaceutical composition. In some embodiments, method 100 may comprise steps of: step 101, step 102, step 103, step 104, step 105, step 106, step 107, step 108, step 109, step 110, and step 111. In some embodiments, step 101 may be a step of prepping a clean work area (e.g., cleaning and/or disinfecting). In some embodiments, step 102 may be a step of using only sterilized and/or depyrogenated equipment and/or tools. In some embodiments, step 103 may be a step of weighing out the applicable APIs; e.g., in a powder hood. In some embodiments, step 104 may be a step of dissolving the weighed out API powders in appropriate solution, such as, but not limited to aqueous solutions, including, but not limited to, sterile water (or WFI). In some embodiments, step 105 may be a step of testing (e.g., via a calibrated pH meter) and adjusting (e.g., via adding acids and/or bases) to a pH of a predetermined target value. In some embodiments, step 106 may be a step of qs ("quantity sufficient") with the appropriate solution (e.g., the sterile water (or the WFI)). In some embodiments, step 107 may be a step of transferring a resulting solution to a compounding aseptic isolator (CAI). In some embodiments, step 108 may be a step of sterile filtering (e.g., a 0.22 micron filter) the resulting solution to yield the given pharmaceutical composition. In some embodiments, step 109 may be a step of QA/QC (quality assurance/quality control) testing, such as bubble point testing, sterility testing, pyrogen testing, endoxin testing, and/or clarity and/or color comparison testing. In some embodiments, step 110 may be a step of filling a final delivery device(s) (or final storage device or final storage container); such as, but not limited to, sterile ophthalmic dropper bottles (e.g., a "drop-tainers," "steri-droppers," or the like), vials, pre-filled syringes, and/or the like. In some embodiments, step 111 may be a step of labeling (e.g., contents, expiration date, lot number, compounding date, and/or the like) and/or storage.

In some embodiments, method 100 may comprise one or more steps from FIG. 1.

Figure 2:
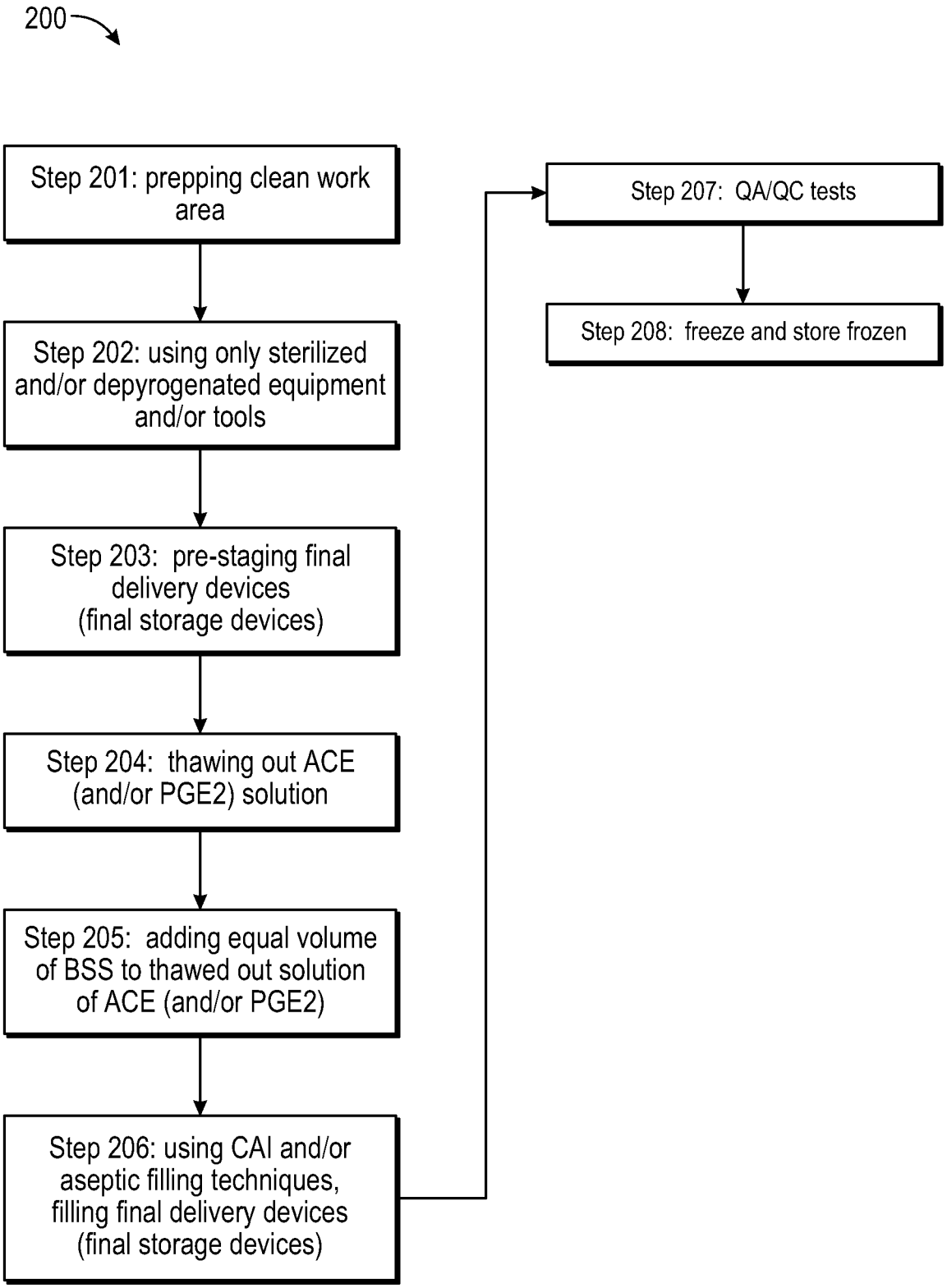
FIG. 2 may depict a flow diagram of another method; wherein this method may comprise steps for compounding and/or filling a particular pharmaceutical composition.

FIG. 2 may depict a flow diagram of a method 200; wherein method 200 may comprise the steps for compounding and/or filling a given pharmaceutical composition. In some embodiments, method 200 may comprise steps of: step 201, step 202, step 203, step 204, step 205, step 206, step 207, and step 208.

In some embodiments, step 201 may be a step of prepping the clean work area (e.g., cleaning and/or disinfecting). In some embodiments, step 202 may be a step of using only sterilized and/or depyrogenated equipment and/or tools. In some embodiments, step 203 may be a step of pre-staging the final delivery devices (or final storage devices). In some embodiments, step 203 may also comprise pre-labeling of these final delivery devices (or final storage devices). In some embodiments, step 204 may be a step of thawing out the ACE (and/or the PGE2) solution using room temperature water bath. In some embodiments, step 205 may be a step of adding an equal volume of the BSS to the thawed out solution of the ACE (and/or the PGE2). In some embodiments, step 206 may be a step of using the CAI and/or aseptic filling techniques, filling the final delivery devices (or final storage devices). In some embodiments, step 207 may be a step of QA/QC (quality assurance/quality control) testing, such as, but not limited to, sterility testing, pyrogen testing, endotoxin testing, clarity testing, and/or color testing. In some embodiments, step 208 may be a step of freezing and storing frozen the filled final delivery devices (or final storage devices).

In some embodiments, method 200 may comprise one or more steps from FIG. 2.

Timolol 0.5%, Brimonidine Tartrate 0.2%, Dorzolamide HCl 2%, and Latanoprost 0.005% Study FIG. 3 through FIG. 9 show study results of a multicenter trial of a pharmaceutical composition comprising timolol maleate 0.5%, brimonidine tartrate 0.2%, and dorzolamide HCl 2%; and a pharmaceutical composition comprising timolol maleate 0.5%, brimonidine tartrate 0.2%, dorzolamide HCl 2%, and latanoprost 0.005%; wherein these two pharmaceutical compositions were used to treat glaucoma, specifically, primary open-angle glaucoma (POAG).

In the United States, glaucoma is primarily controlled with topical eye drop therapy with the goal of reducing intraocular pressure (IOP) by 30%. To achieve this goal up to 40% of glaucoma patients will require more than one type topical eye drop medication; i.e., currently the glaucoma patients must use multiple and different eye drop medications to achieve this goal and this presents a patient compliance problem. To increase patient compliance it is desirable to provide only one eye drop delivery device that contains one or more glaucoma medications.

A single bottle of compounded combination glaucoma medication containing multiple molecules (such as, but not limited to timolol maleate, brimonidine tartrate, dorzolamide, and latanoprost in some formulations) may accomplish the necessary 30% IOP reduction while improving patient compliance, simplifying dosing schedule, reducing preservatives, and providing potential cost savings.

A purpose of this study was to demonstrate non-inferiority as well as the safety and efficacy of a compounded combination IOP lowering medication (i.e., the two pharmaceutical compositions used in this study in the IP Group) in the treatment of glaucoma in patients who are currently using three or more separate glaucoma medications (in three or more dropper bottles) who exhibit difficulty with patient compliance and/or have elevated intraocular pressure (IOP).

With respect to the method of this study, this was a randomized multicenter, observer masked study of parallel-groups with primary open-angle glaucoma (POAG). Inclusion criterial required patients to be currently taking at least three IOP different and separate lowering medications. Further with respect to the design of this study, this study utilized randomized 1:1, double masked, prospective, multicenter study of 53 subjects with POAG.

The two pharmaceutical compositions tested in the IP Group were: timolol maleate 0.5%, brimonidine tartrate 0.2%, dorzolamide hydrochloride 2%, with BAK 0.001% qAM; and timolol maleate 0.5%, brimonidine tartrate 0.2%, dorzolamide hydrochloride 2%, latanoprost 0.005%, with BAK 0.001% qhs.

Whereas, in the control group, consisted of patients (subjects) continuing to use their current multiple eye drop therapy of at least three separate and different eye drop glaucoma medications (also known as the multiple drops group).

Subjects were seen for evaluation at baseline and on days 7±2, 30±7, 60±7, and 90±7 following the initial visit and randomization arm was masked.

A primary outcome measurement was IOP change, and secondary measurements included corneal staining, patient-reported symptoms, and visual acuity.

A study eye was defined as the eye with the highest morning IOP score at the screening visit (baseline) and was the primary eye used for analyses. Patients without baseline or any post baseline IOP data were excluded from analyses.

Primary Outcome: Non-inferiority as assessed by upper bound of 2-sided 95% confidence interval for the between-group difference in mean change from baseline at all time points.

Analysis of covariance, ANCOVA, was used to analyze continuous measures, with fixed effects for treatment and investigative site, and baseline as a continuous covariate.

With respect to this study's results, see FIG. 3 through FIG. 9.

FIG. 3 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 3 may depict some baseline characteristics.

Figure 4:
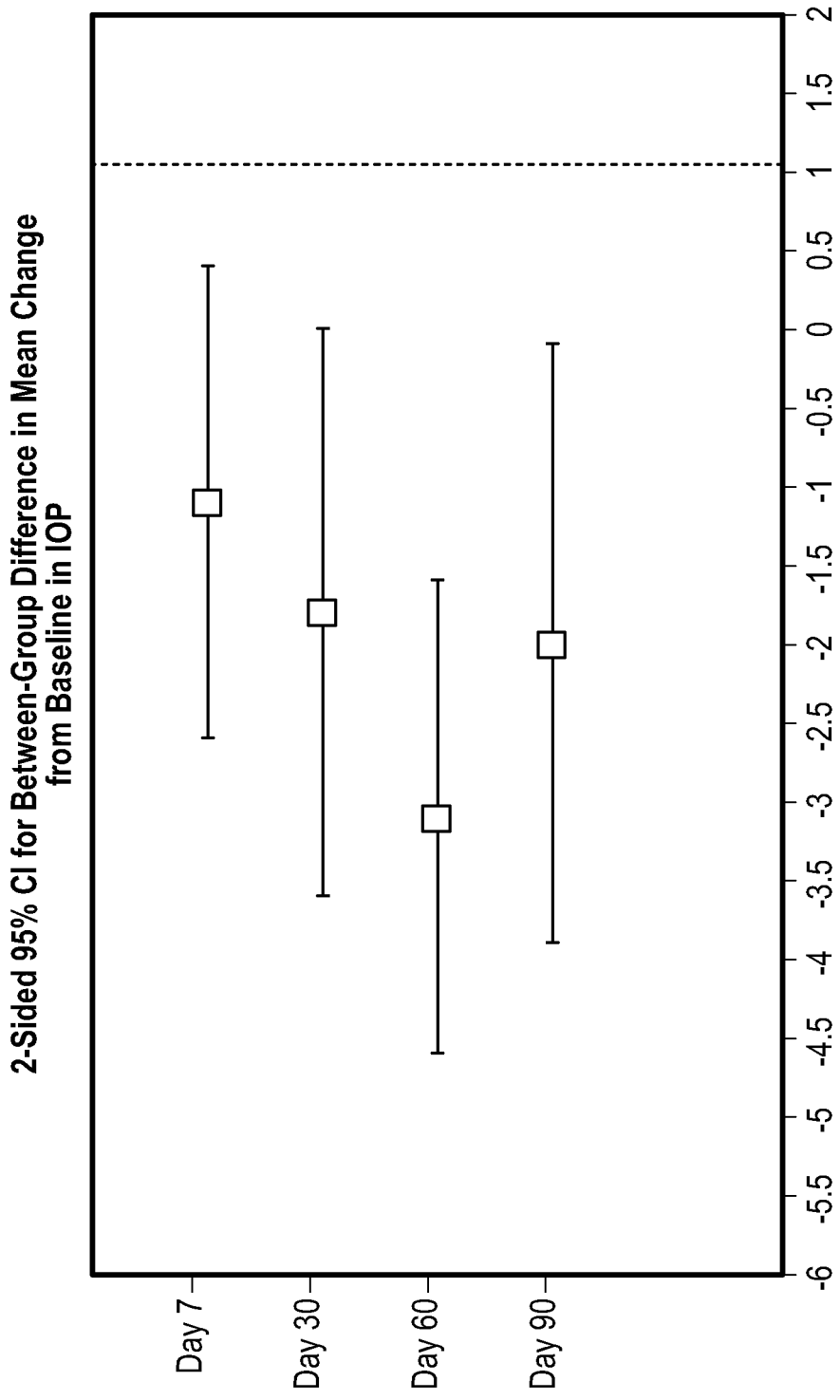
FIG. 4 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 4 may depict a 2-sided 95% confidence interval (CI).

FIG. 4 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 4 may depict a 2-sided 95% confidence interval (CI).

Figure 5:
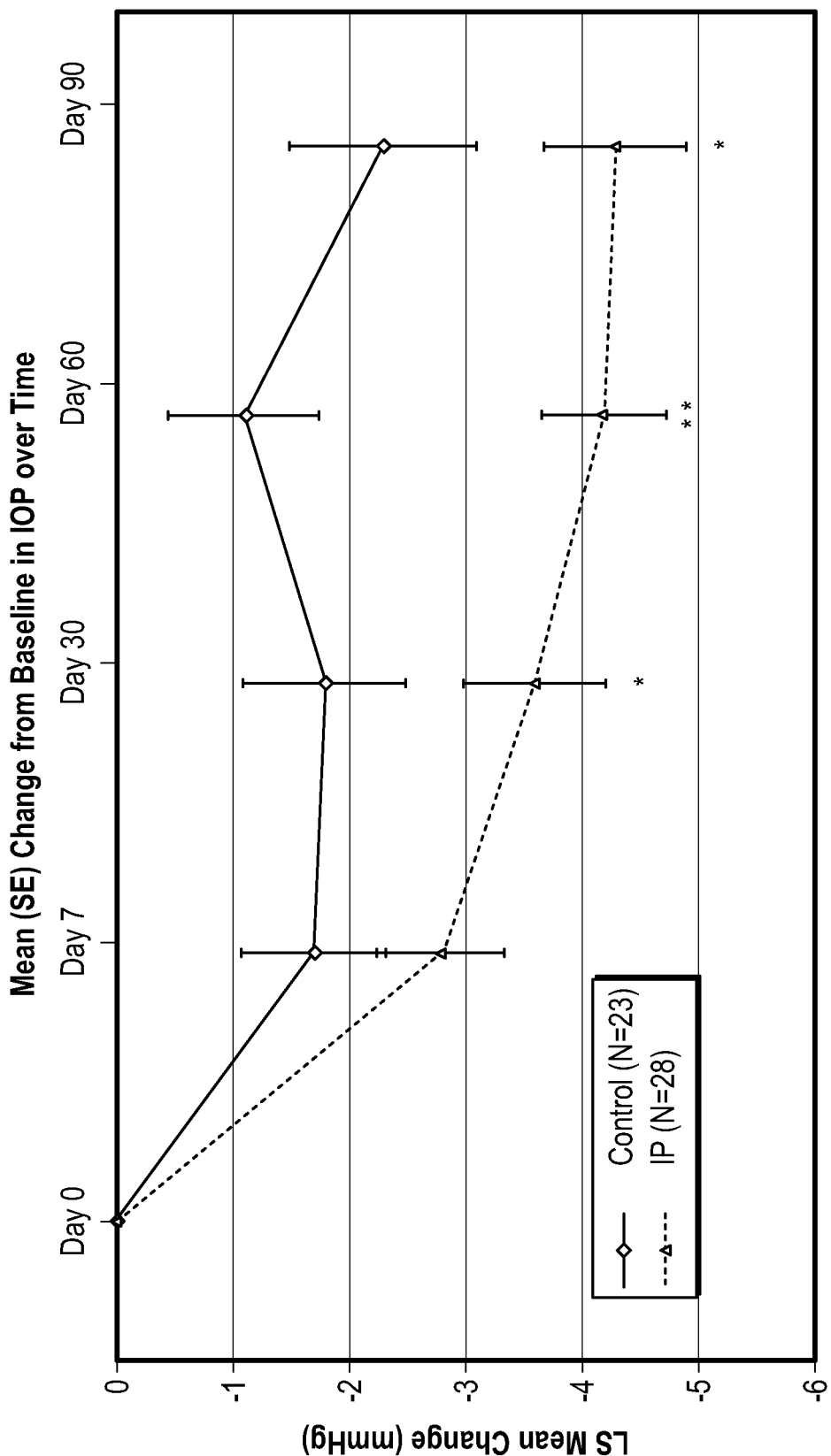
FIG. 5 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 5 may depict mean change from baseline in IOP (intraocular pressure) over time.

FIG. 5 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 5 may depict mean change from baseline in IOP (intraocular pressure) over time.

FIG. 6 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 6 may depict morning IOP change from baseline.

Figure 7:
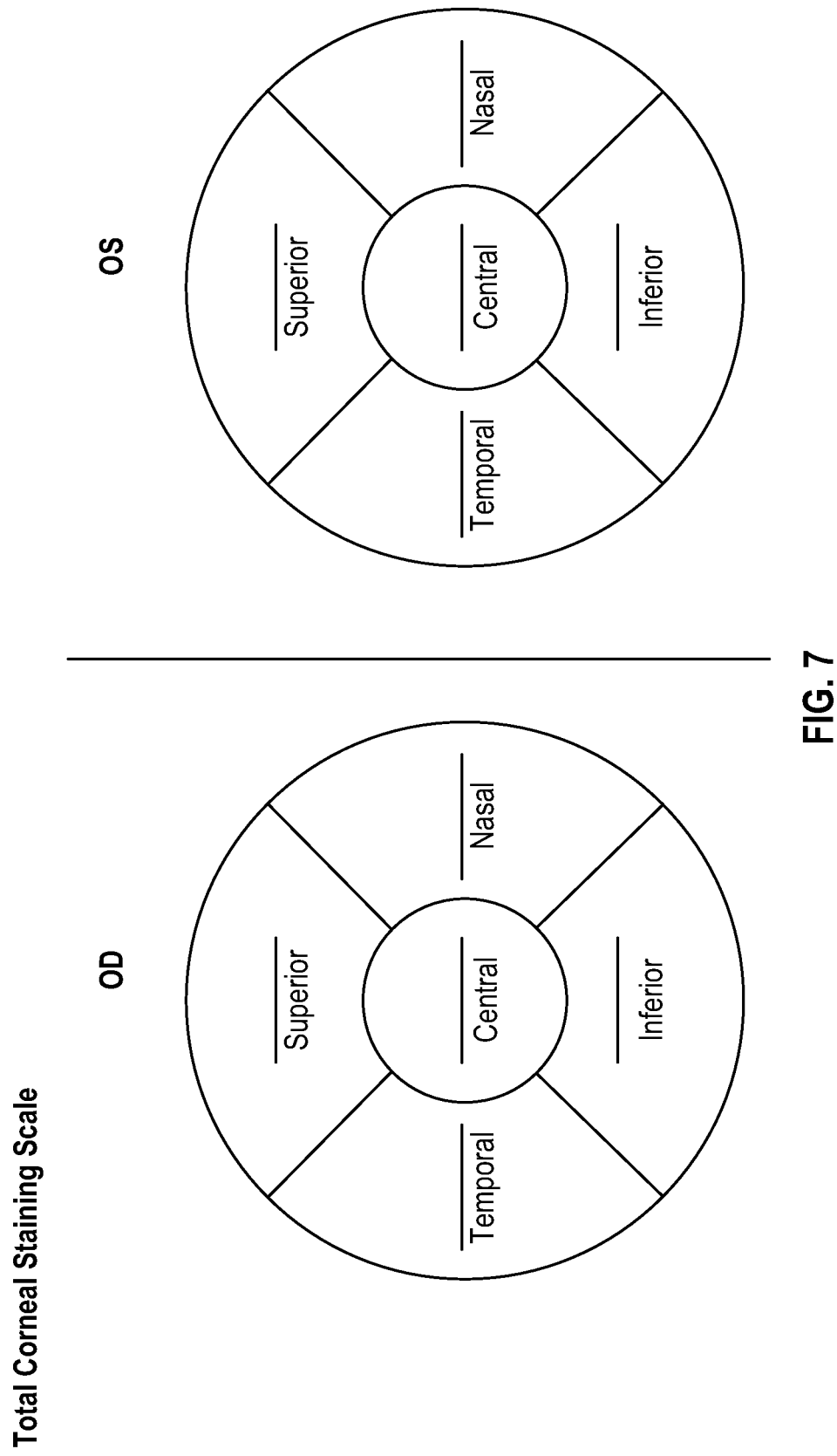
FIG. 7 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 7 may depict total corneal staining scale (TCS) information.

FIG. 7 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 7 may depict total corneal staining scale (TCS) information.

Figure 8:
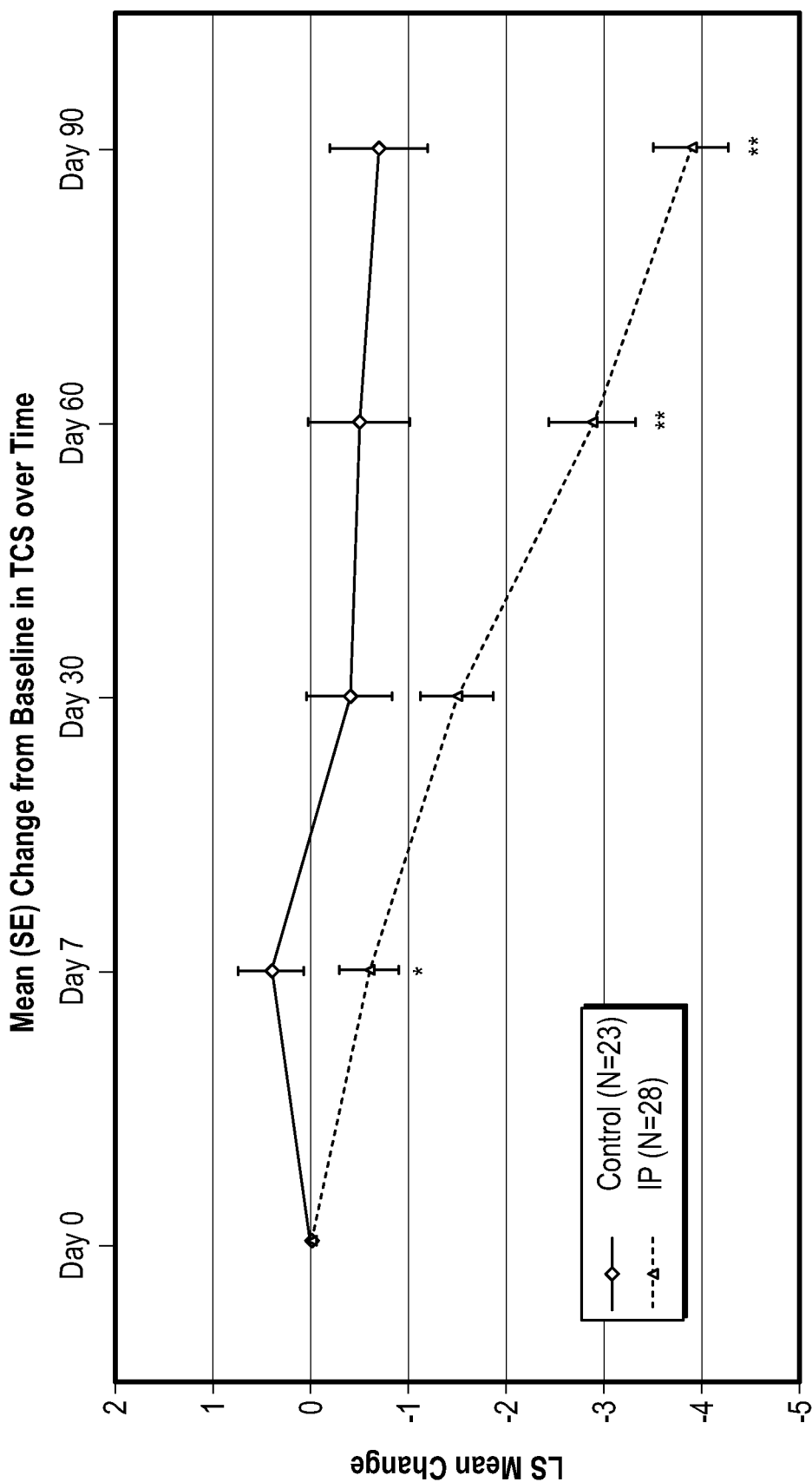
FIG. 8 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 8 may depict mean change from baseline in TCS over time.

FIG. 8 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 8 may depict mean change from baseline in TCS over time.

FIG. 9 may depict a table from a study on a pharmaceutical composition comprising timolol maleate 0.5%, brimonidine tartrate 0.2%, and dorzolamide HCl 2%; and on a pharmaceutical composition comprising timolol maleate 0.5%, brimonidine tartrate 0.2%, dorzolamide HCl 2%, and latanoprost 0.005%; wherein FIG. 9 may depict visual acuity change from baseline.

Some of these results may be summarized as follows:
- 29 patients randomized to IP Group and 24 to Control Group;
- 2 patients (one in Control and one in IP Group) withdrew consent and discontinued early; 2 with no post-baseline data;
- Morning IOP study eye: upper limit of 95% CI was <1.0 mmHg at all time points (days 7, 30, 60 and 90) demonstrating non-inferiority of IP to Control:
  - Upper limit of 95% CI<0 at days 30, 60 and 90 indicating superiority of IP;
  - Additionally, upper limit <1 for morning fellow eye IOP and both eyes for afternoon IOP at all time points;
- Mean decreases from baseline in Total CFS were greater in the IP group and significantly so at days 7, 60 and 90 (study eye and fellow eye);
- Changes from baseline in visual acuity were similar between IP and Control (study eye).

With respect to Total Corneal Staining (TCS) Results see FIG. 7 and FIG. 8. Summarizing these TCS results:
- 82% of subjects assigned to IP and 29% of control subjects showed an improvement from baseline to Day 60;
- 89% of subjects assigned to IP and 47% of control subjects showed an improvement from baseline to Day 90;
- 54% of subjects assigned to IP and 5% of control subjects improved at least 4 points from baseline to Day 90;
- 2 subjects assigned to IP had a 10 point improvement from baseline by Day 90.

Discussion of this Study

In this study, we evaluated a compounded medication containing three or four topical intraocular pressure-lowering molecules (timolol, brimonidine, dorzolamide and latanoprost) (the IP Group) and found that these tested pharmaceutical compositions with either the three or the four intraocular pressure-lowering molecules (timolol, brimonidine, dorzolamide and latanoprost) were not inferior compared to the standard regimen of the Control Group.

At days 30, 60, and 90 of this study, the IP Group showed a greater absolute intraocular pressure reduction than the control. That is, the IP Group showed greater efficacy as compared against the Control Group.

We found no evidence of additional safety problems associated with the use of IP Group versus the standard regimen (Control Group).

Mean differences in corneal fluorescein staining showed that, compared with the standard regiment (Control Group), the IP Group was associated with lower levels of corneal surface lesions. These differences were significant at Days 7, 60, and 90. This may be potentially be explained by the lower levels of preservatives in the IP Group compared to the standard regimen (Control Group).

Conclusions of this Study

In this study, the IP Group was not only not inferior to standard multiple bottle medication regimen (Control Group), but was found to be superior in efficacy. Corneal fluorescein staining showed improvement in the IP Group compared to the group on the standard regimen (Control Group).

There was no evidence of additional safety problems from the compounded IP Group compared to the standard regimen (Control Group).

Inherently there are many benefits to combining three or such four medications (timolol, brimonidine, dorzolamide and latanoprost) into a single eye dropper bottle. These benefits include greater patient compliance, increased efficacy, a lower amount of preservative exposure to the patient, the use of fewer bottles, an easier dosing schedule, and potential cost savings.

Prednisolone PO4 1% and Gatifloxacin 0.5% Study

FIG. 10 through FIG. 16 show study results of a multi-center trial of efficacy and tolerability a pharmaceutical composition comprising prednisolone PO4 (phosphate) 1% and gatifloxacin 0.5%; wherein this pharmaceutical composition was administered as a topical prophylaxis (e.g., as eye drops) after laser vision corrective surgery (e.g., LASIK).

A purpose of this study may have been to demonstrate non-inferiority of using multiple drugs (APIs) in a deliver device (e.g., eye dropper) in the context of post-operative care of an eye after laser eye surgery (e.g., laser-assisted in-situ keratomileusis [LASIK]).

With respect to methodology of this study, this was a randomized 1:1, investigator masked, prospective, multi-center study of 101 refractive surgical eyes who underwent LASIK.

The tested pharmaceutical composition, noted as the IG Group in figures FIG. 10 through FIG. 16, comprised prednisolone phosphate 1%, gatifloxacin 0.5% QID×1 week.

Whereas, the Multiple Drops Group (the Control Group) was two separate and different eye droppers of: (1) prednisolone Acetate 1% QID×1 week; and (2) gatifloxacin Ophthalmic Solution 0.5% QID×1.

Primary Endpoint: Non-inferiority of the prevention of infection and inflammation over 1 month as assessed by upper bound of 2-sided 95% confidence interval for the between-group difference in mean change from baseline. Analysis of covariance, ANCOVA, was used to analyze continuous measures, with fixed effects for treatment and investigative site, and baseline as a continuous covariate. No adjustment made to p-values due to multiple comparisons.

Secondary Endpoint: Refractive Outcomes, and clinical biomicroscopic examination; such as, corneal staining, and change in IOP.

Results of this study may depicted in figures FIG. 10 through FIG. 16.

FIG. 10 may depict a table from a study on a pharmaceutical composition comprising prednisolone PO4 (phosphate) 1% and gatifloxacin 0.5%; wherein FIG. 10 may depict UCDVA (uncorrected distance visual acuity) frequencies.

FIG. 11 may depict a table from a study on a pharmaceutical composition comprising prednisolone PO4 (phosphate) 1% and gatifloxacin 0.5%; wherein FIG. 11 may depict UCDVA (uncorrected distance visual acuity) frequencies.

FIG. 12 may depict a table from a study on a pharmaceutical composition comprising prednisolone PO4 (phosphate) 1% and gatifloxacin 0.5%; wherein FIG. 12 may depict UCVA (uncorrected visual acuity) outcomes summary.

FIG. 13 may depict a table from a study on a pharmaceutical composition comprising prednisolone PO4 (phosphate) 1% and gatifloxacin 0.5%; wherein FIG. 13 may depict AC Cell results.

FIG. 14 may depict a table from a study on a pharmaceutical composition comprising prednisolone PO4 (phosphate) 1% and gatifloxacin 0.5%; wherein FIG. 14 may depict AC flare results.

FIG. 15 may depict a table from a study on a pharmaceutical composition comprising prednisolone PO4 (phosphate) 1% and gatifloxacin 0.5%; wherein FIG. 15 may depict total corneal staining (TCS) results.

FIG. 16 may depict a table from a study on a pharmaceutical composition comprising prednisolone PO4 (phosphate) 1% and gatifloxacin 0.5%; wherein FIG. 16 may depict IOP (intraocular pressure) change from baseline.

Some of these results may be summarized as follows:
Study eye was defined as the eye with the highest total corneal staining score at the screening visit (baseline) and was used for analyses;
No significant differences between IP Group and Control Group at any visit as measured by AC cell, AC flare, and change from baseline in IOP, corneal staining, and visual acuity in the study eye;
Corneal Staining: upper limit of 95% CI was <0.2 at Day 30 demonstrating non-inferiority of IP Group to Control Group on this measure;
Mean decreases from baseline to Day 30 in Corneal Staining and IOP were greater in the IP Group, demonstrating greater efficacy of the IP Group over the Control Group;
Changes from baseline in visual acuity were similar between IP Group and Control Group;
All patients scored 0 for AC cell and AC flare at Day 30;
There was no post-operative complication in either group; and
There was no significant post-operative discomfort in either group at all time periods.

Conclusions of this Study

This multicenter, masked, prospective study demonstrated compounding combination medication (the IP Group) was non-inferior to conventional brand name medication (the Control Group). In fact, the IP Group was shown to be superior to the Control Group, e.g., at Day 30 and with respect to metrics of corneal staining and IOP.

Patient compliance may be improved with this combination therapy (the IP Group) and has been shown to be safe and therapeutically equivalent or superior to conventional multiple medication therapy (Control Group) for postoperative management following LASIK.

Amniotic Cytokines Extract (ACE) Study

FIG. 17 through FIG. 23 show study results of a pharmaceutical composition comprising amniotic cytokine extract in an eye dropper delivery device for the treatment of dry eyes. A purpose of this study may have been to evaluate an amniotic cytokine extract (ACE) pharmaceutical composition in the treatment of dry eye disease.

Dry eye disease (DES) may be a complex and multifactorial condition—making it difficult to test with existing molecules. Dry eye disease may involve multiple inflammatory pathways. There may be a disconnect between when signs and symptoms can occur, which may further complicate diagnosis. There is a need for novel therapies for treating dry eye disease.

The pharmaceutical composition used in this study comprised an extract of amniotic cytokines and was administered via eye drops. This extract of amniotic cytokines may have comprised active cytokines, growth factors, and anti-inflammatory molecules. This extract of amniotic cytokines may have comprised over 120 active cytokines. This extract of amniotic cytokines may have comprised PGE2. This extract of amniotic cytokines may have comprised GDF11. This extract of amniotic cytokines may have comprised WNT4. This extract of amniotic cytokines may have comprised Thrombospondin-1. PGE2 may promote wound healing. GDF11 may promote inflammation modulation. WNT4 may promote regeneration. Thrombospondin-1 may modulate WBC, as well as dendritic cells/APC that stimulate T cell proliferation. This pharmaceutical composition may have been titrated to a specific concentration of PGE2.

A proprietary cryopreservation technique may have been used to harvest this cytokine extract from amniotic tissue in a manner that preserves important anti-inflammatory molecules for treating ocular surface inflammation that mediates dry eye disease.

Methods of this Study

This study included a retrospective chart review including 53 patients from 7 US clinicians who treated symptomatic dry eye disease patients with the pharmaceutical composition comprising the amniotic cytokine extract (ACE) described above, administered as eye drops.

All patients in the study used this pharmaceutical composition of ACE as one drop twice daily for 12 weeks.

The study eye was defined as the eye with the highest total corneal staining score (TCSS) at baseline.

Following parameters were assessed at baseline, 4 weeks, 8 weeks and 12 weeks after treatment:
Visual acuity;
Symptom score assessed as Eye Dryness Score (EDS) based on a visual analog scale (0-100);
Conjunctival and corneal staining scores using lissamine green and sodium fluorescein; and
Adverse events.

Results of this Study

Results of this study may depicted in figures FIG. 17 through FIG. 23.

FIG. 17 may depict a table from a study on a pharmaceutical composition comprising PGE2 and active cytokines from amniotic cytokine extract; wherein FIG. 17 may depict summary of week 4 study results.

FIG. 18 may depict a table from a study on a pharmaceutical composition comprising PGE2 and active cytokines from amniotic cytokine extract; wherein FIG. 18 may depict summary of week 12 study results.

Figure 19:
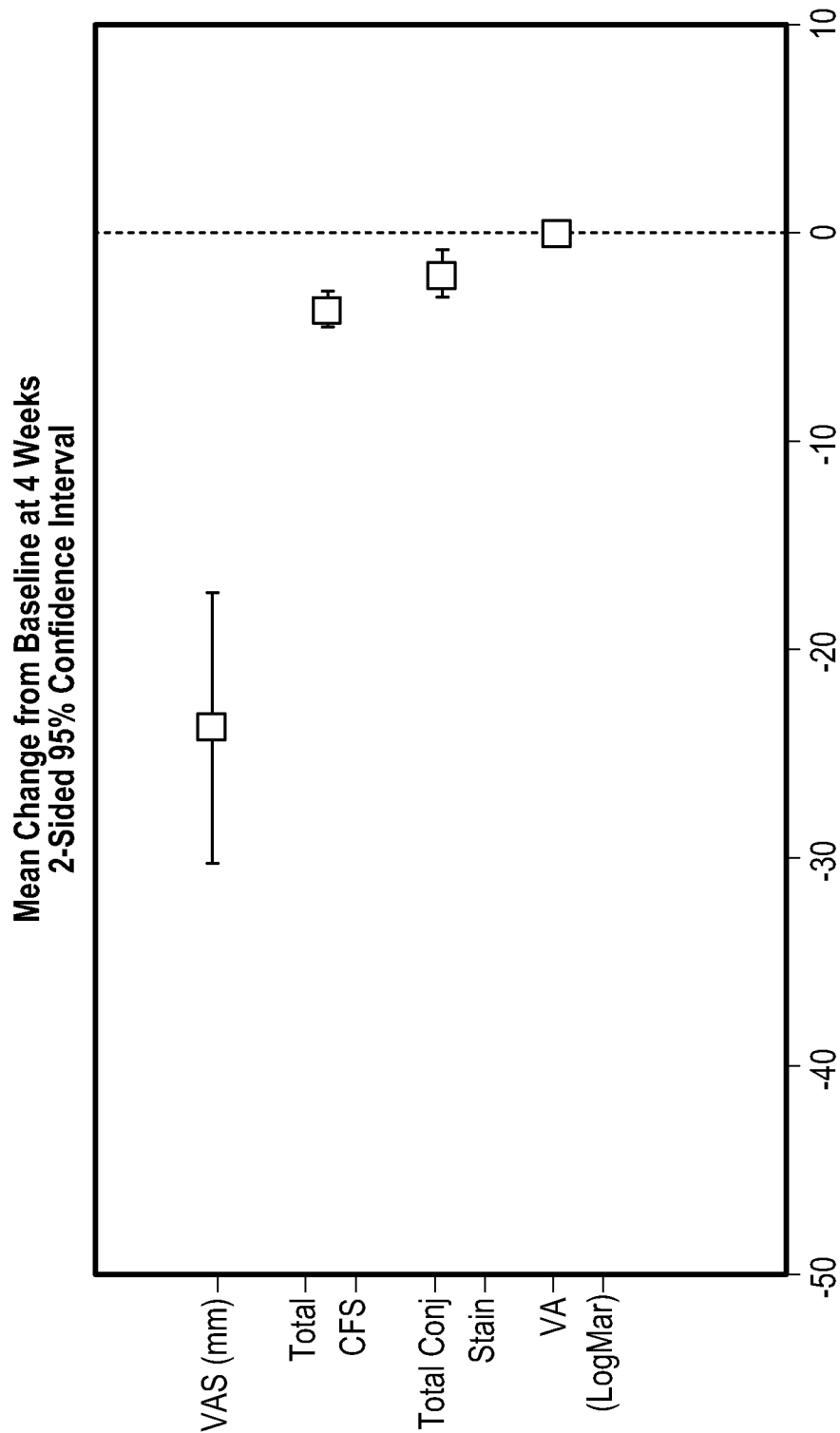
FIG. 19 may depict a table from a study on a pharmaceutical composition comprising PGE2 and active cytokines from amniotic cytokine extract; wherein FIG. 19 may depict mean change from baseline at 4 weeks, 2-sided 95% confident interval (CI).

FIG. 19 may depict a table from a study on a pharmaceutical composition comprising PGE2 and active cytokines from amniotic cytokine extract; wherein FIG. 19 may depict mean change from baseline at 4 weeks, 2-sided 95% confident interval (CI).

Figure 20:
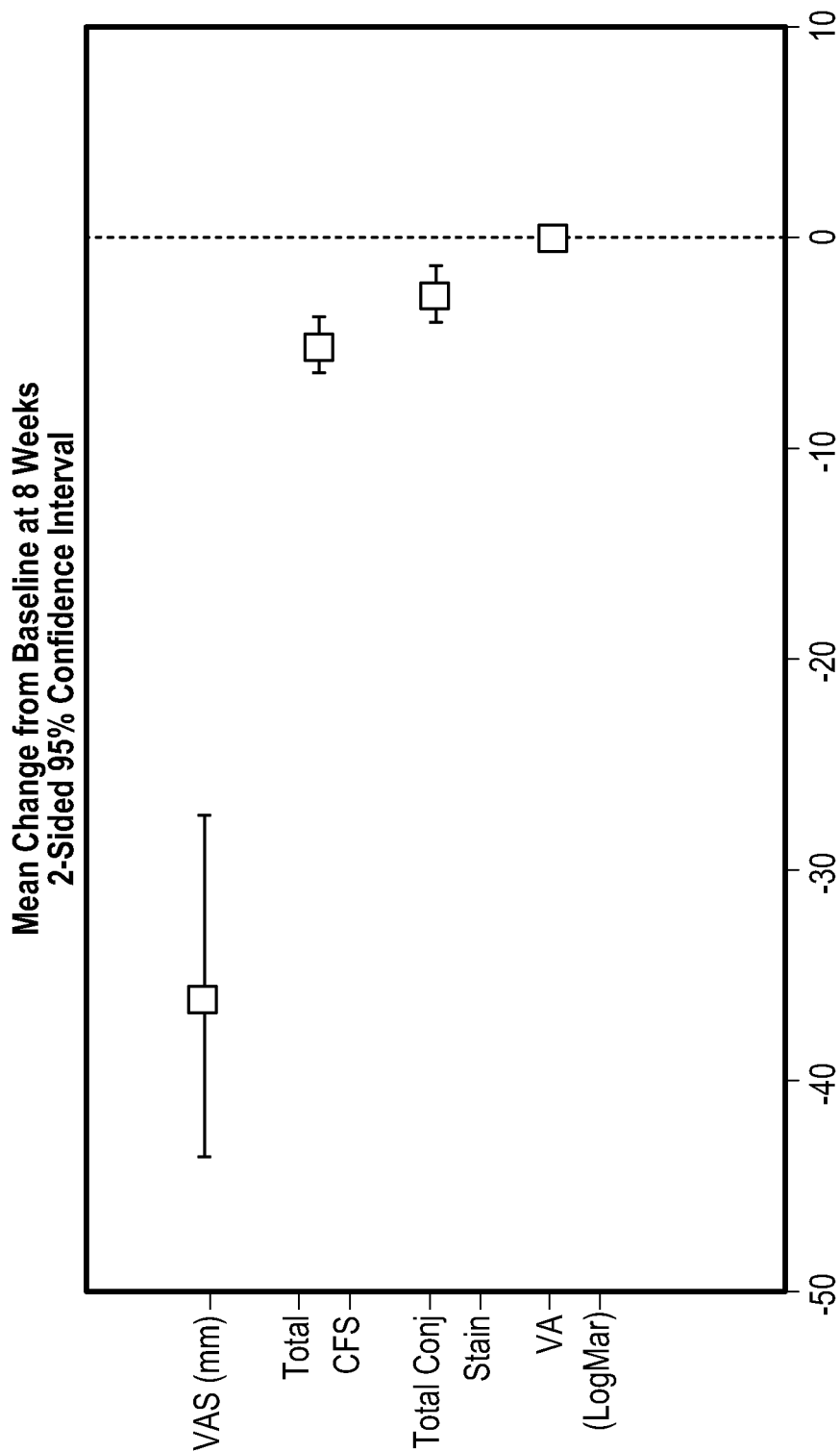
FIG. 20 may depict a table from a study on a pharmaceutical composition comprising PGE2 and active cytokines from amniotic cytokine extract; wherein FIG. 20 may depict mean change from baseline at 8 weeks, 2-sided 95% confident interval (CI).

FIG. 20 may depict a table from a study on a pharmaceutical composition comprising PGE2 and active cytokines from amniotic cytokine extract; wherein FIG. 20 may depict mean change from baseline at 8 weeks, 2-sided 95% confident interval (CI).

Figure 21:
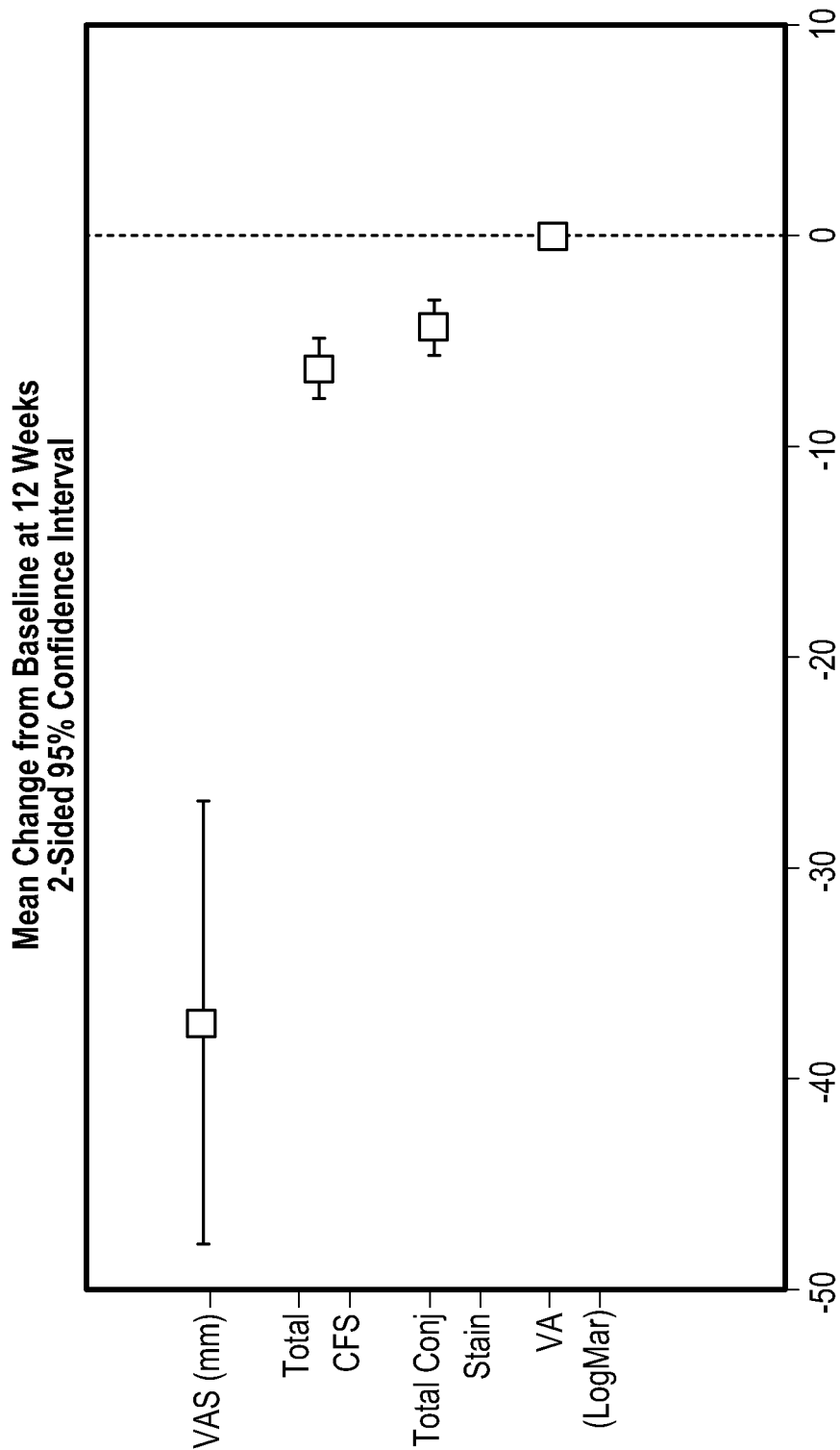
FIG. 21 may depict a table from a study on a pharmaceutical composition comprising PGE2 and active cytokines from amniotic cytokine extract; wherein FIG. 21 may depict mean change from baseline at 12 weeks, 2-sided 95% confident interval (CI).

FIG. 21 may depict a table from a study on a pharmaceutical composition comprising PGE2 and active cytokines from amniotic cytokine extract; wherein FIG. 21 may depict mean change from baseline at 12 weeks, 2-sided 95% confident interval (CI).

Figure 22:
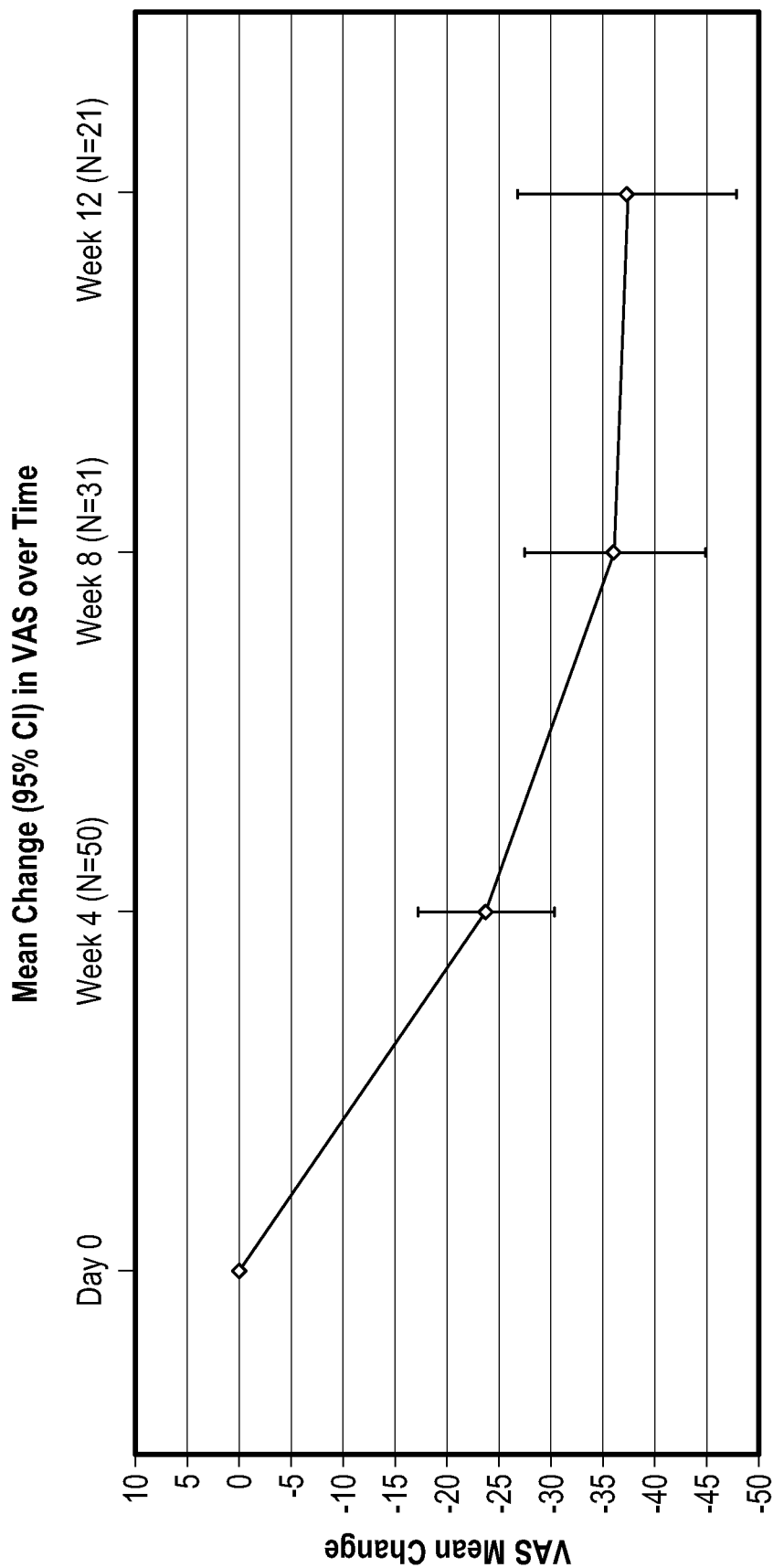
FIG. 22 may depict a table from a study on a pharmaceutical composition comprising PGE2 and active cytokines from amniotic cytokine extract; wherein FIG. 22 may depict mean change (95% CI) in VAS over time.

FIG. 22 may depict a table from a study on a pharmaceutical composition comprising PGE2 and active cytokines from amniotic cytokine extract; wherein FIG. 22 may depict mean change (95% CI) in VAS over time.

Figure 23:
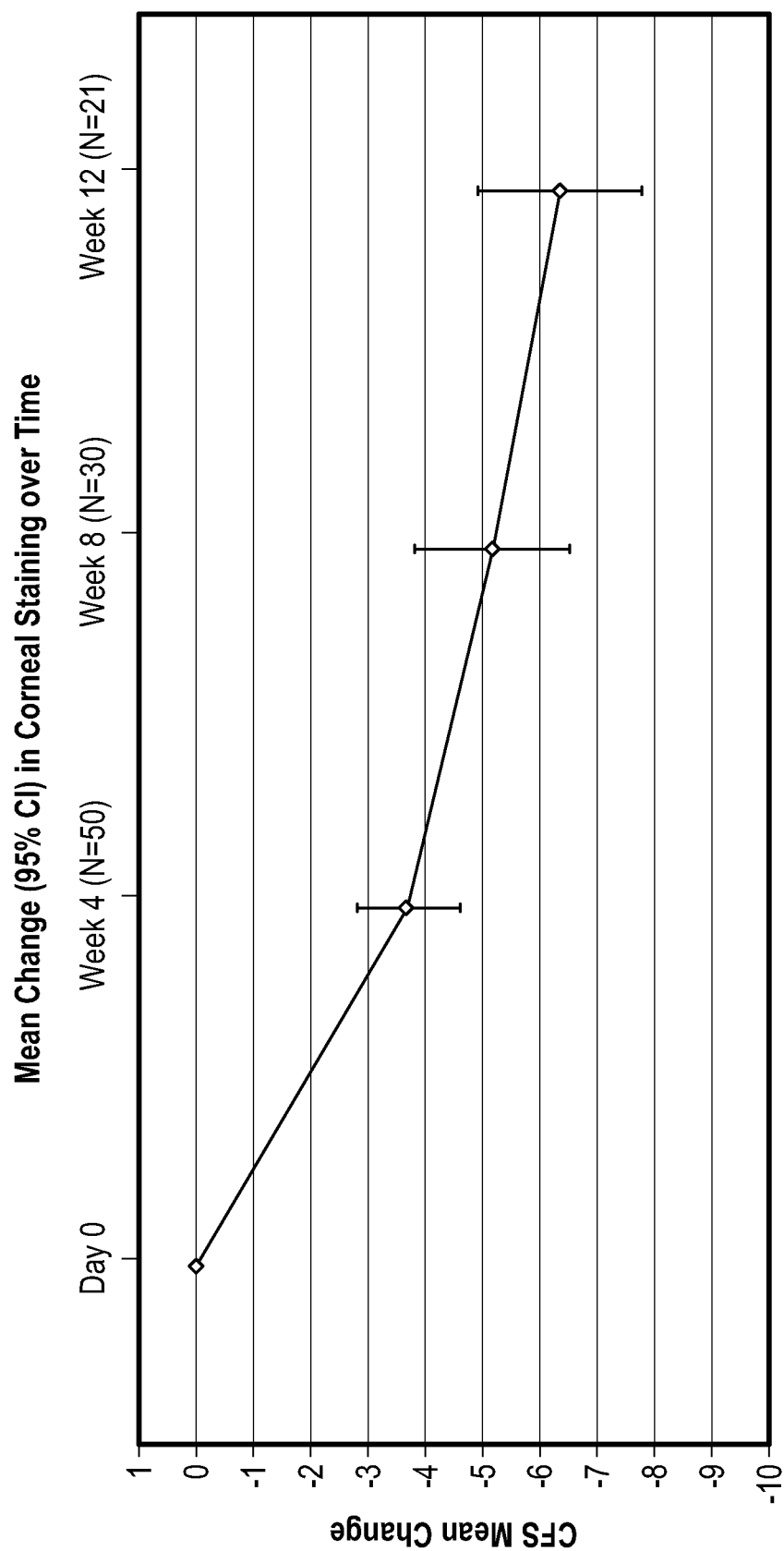
FIG. 23 may depict a table from a study on a pharmaceutical composition comprising PGE2 and active cytokines from amniotic cytokine extract; wherein FIG. 23 may depict mean change (95% CI) in corneal staining over time.

FIG. 23 may depict a table from a study on a pharmaceutical composition comprising PGE2 and active cytokines from amniotic cytokine extract; wherein FIG. 23 may depict mean change (95% CI) in corneal staining over time.

Some of these Results May be Summarized as Follows:
Visual acuity remained unchanged in all patients;
There were no adverse events reported;
Primary endpoints:
  Mean Eye Dryness Score improved over 12 weeks from 68.3 to 36.7 ($p<0.001$);
    94% of subjects showed an improvement on VAS score from baseline;
  Mean Total Corneal Staining Score improved over 12 weeks from 9.4 to 1.3 ($p<0.001$);
    95% of subjects sowed an improvement of at least 50% on TCS from baseline;
Secondary endpoints:
  Mean Total Conjunctival Staining Score improved from 5.9 to 1.7 ($p<0.001$);
    95% of subjects showed an improvement in total conjunctival staining from baseline.
An unexpected result of eyelash growth was also seen.

Conclusions of this Study

Pharmaceutical compositions comprising amniotic cytokines extract (ACE) as described, is a safe, effective, and novel therapy for the treatment of dry eye disease.

Key preservation techniques allow retention of beneficial cytokine activity.

This pharmaceutical composition comprising amniotic cytokines extract (ACE) may also promote and/or facilitate eyelash growth.

In some embodiments, any of the above discussed pharmaceutical compositions may be ophthalmic solutions, used to treat the eye, at the eye, in the eye, and/or around the eye.

Note that the various acids and bases used in these pharmaceutical compositions (e.g., to adjust pH and/or tonicity during compounding) may not exist as acids nor bases once used in the given pharmaceutical composition, as such acids and bases may dissociate in solution into water and their ionic forms (e.g., $Na^+$, $Cl^-$, etc.).

In preparing the above discussed pharmaceutical compositions, in weighing out dry (e.g., power form) of a given API for a given target concentration (e.g., by weight by volume, w/v), it may be necessary to use the source API's certificate of analysis (CofA) and to use the molecular weight of that given API to calculate a multiplication factor or correction factor. For example, use of a correction factor (multiplication factor) may be needed because: (1) the given API is hygroscopic, taking some degree of water, wherein the CofA should report that amount of water and should be accounted for; and/or (2) assessment of a salt, acid, and/or a base form of the given API may be required depending upon a standard of reference for the given API (e.g., as specified by the USP), molecular weight of a salt form will be different from that of its corresponding free base or free acid form, and calculation of such different molecular weight ratios may determine this correction factor (multiplication factor). For example, pharmaceutical compositions including prednisolone PO4 may require such a correction; whereas, pharmaceutical compositions including ketorolac tromethamine may not require such a correction. For example, pharmaceutical compositions including timolol and/or brimonidine tartrate may require such a correction. For example, pharmaceutical compositions including moxifloxacin and/or dexamethasone phosphate may require such a correction. For example, pharmaceutical compositions including gatifloxacin may require such a correction. For example, pharmaceutical compositions including bromfenac may require such a correction.

Compositions (e.g., pharmaceutical compositions), methods for treating various issues of the eyes, and methods of preparing such compositions have been described. The foregoing description of the various exemplary embodiments of the invention has been presented for the purposes of illustration and disclosure. It is not intended to be exhaustive or to limit the invention to the precise form disclosed. Many modifications and variations are possible in light of the above teaching without departing from the spirit of the invention.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

What is claimed is:

1. A method for treating an ocular condition of an eye; comprising administering a pharmaceutical composition at, in, or around the eye via a delivery device and per a predetermined dosing regimen, wherein:
   the pharmaceutical composition is free of preservatives;
   the pharmaceutical composition comprises one of:
   (1) phenylephrine HCl 1.5%, lidocaine HCl 1%, and ketorolac tromethamine 0.3%; or
   (2) phenylephrine HCl 1.5%, lidocaine HCl 1%, and bromfenac 0.01%;
   wherein these percentages are with respect to weight per volume; and
   wherein the ocular condition is glaucoma, care after cataract surgery, care after LASIK surgery, care for a retina of the eye after cataract surgery, care for a retina of the eye after retina surgery, in preparation for an intraocular procedure, or during the intraocular procedure.

2. The method according to claim 1, wherein the delivery device is an eye dropper or a syringe for intra-cameral injection.

3. The method of claim 2, wherein the delivery device is the eye dropper, wherein the eye dropper is a light resistant bottle.

4. The method according to claim 1, wherein the predetermined dosing regimen is once per day, twice per day, three times per day, once every other day, once per week, once every other week, or once monthly.

5. The method according to claim 1, wherein the pharmaceutical composition comprises phenylephrine HCl 1.5%, lidocaine HCl 1%, and ketorolac tromethamine 0.3%.

6. The method of claim 5, wherein the pharmaceutical composition has a pH of 6.5.

7. The method according to claim 1, wherein the pharmaceutical composition comprises phenylephrine HCl 1.5%, lidocaine HCl 1%, and bromfenac 0.01%.

8. The method of claim 7, wherein the pharmaceutical composition has a pH of 7.0 to 7.2.

9. The method of claim 1, wherein the ocular condition is in preparation for the intraocular procedure or during the intraocular procedure.

10. The method of claim 9, wherein the intraocular procedure is cataract surgery.

11. The method of claim 10, wherein the method further reduces post-operation infections after the cataract surgery.

12. The method of claim 10, wherein the method further improves the speed of recovery and quality of vision improvement of the cataract surgery.

13. The method of claim 1, wherein the ocular condition is the care after cataract surgery, the care after LASIK surgery, the care for a retina of the eye after cataract surgery, or the care for a retina of the eye after retina surgery.

14. The method of claim 1, wherein the method reduces post-operation infections after the cataract surgery, the LASIK surgery, or the retina surgery.

15. The method of claim 1, wherein the method improves the speed of recovery and quality of vision improvement of the cataract surgery, the LASIK surgery, or the retina surgery.

16. The method of claim 1, wherein the pharmaceutical composition is stored at room temperature.

17. The method according to claim 1, wherein the pharmaceutical composition has a beyond-use date of at least 180 days.

* * * * *